United States Patent
Tokita

(10) Patent No.: US 8,712,495 B2
(45) Date of Patent: Apr. 29, 2014

(54) DEVICE FOR ACCURATELY MEASURING CONCENTRATION OF COMPONENT IN BLOOD AND CONTROL METHOD OF THE DEVICE

(75) Inventor: Muneo Tokita, Nagaokakyo (JP)

(73) Assignee: Omron Healthcare Co., Ltd., Kyoto (JP)

( * ) Notice: Subject to any disclaimer, the term of this patent is extended or adjusted under 35 U.S.C. 154(b) by 334 days.

(21) Appl. No.: 12/775,642

(22) Filed: May 7, 2010

(65) Prior Publication Data

US 2010/0234702 A1 Sep. 16, 2010

Related U.S. Application Data

(63) Continuation of application No. PCT/JP2008/070034, filed on Nov. 4, 2008.

(30) Foreign Application Priority Data

Nov. 9, 2007 (JP) .................................. 2007-292403

(51) Int. Cl.
*A61B 5/05* (2006.01)
(52) U.S. Cl.
USPC ............ 600/346; 600/306; 600/309; 600/345
(58) Field of Classification Search
None
See application file for complete search history.

(56) References Cited

U.S. PATENT DOCUMENTS

| | | | | |
|---|---|---|---|---|
| 5,036,861 A | * | 8/1991 | Sembrowich et al. | 600/573 |
| 5,458,140 A | * | 10/1995 | Eppstein et al. | 600/573 |
| 5,638,815 A | * | 6/1997 | Schoendorfer | 600/346 |
| 5,782,871 A | | 7/1998 | Fujiwara et al. | |
| 5,788,688 A | * | 8/1998 | Bauer et al. | 606/1 |
| 6,045,541 A | | 4/2000 | Matsumoto et al. | |
| 8,160,671 B2 | * | 4/2012 | Kamath et al. | 600/347 |
| 2005/0106713 A1 | | 5/2005 | Phan et al. | |
| 2006/0116563 A1 | * | 6/2006 | Asano et al. | 600/319 |
| 2007/0179371 A1 | * | 8/2007 | Peyser et al. | 600/347 |
| 2007/0213600 A1 | * | 9/2007 | John et al. | 600/300 |

FOREIGN PATENT DOCUMENTS

| | | |
|---|---|---|
| JP | 04-028343 A | 1/1992 |
| JP | 09-033532 A | 2/1997 |
| JP | 2793140 B2 | 9/1998 |
| JP | 2964942 B2 | 10/1999 |
| JP | 2985816 B2 | 12/1999 |
| JP | 2007-503958 A | 3/2007 |

OTHER PUBLICATIONS

Official Communication issued in corresponding Japanese Patent Application No. 2007-292403, mailed on Feb. 7, 2012.
Official Communication issued in International Patent Application No. PCT/JP2008/070034, mailed on Dec. 16, 2008.

(Continued)

*Primary Examiner* — Michael Kahelin
*Assistant Examiner* — Mitchell Alter
(74) *Attorney, Agent, or Firm* — Keating & Bennett, LLP

(57) ABSTRACT

A measurement device includes an electronic component device, a perspiration acceleration device, and a perspiration collection device. The perspiration acceleration device or the perspiration collection device is removably coupled to the electronic component device. The electronic component device is attached to a measurement site with a belt. A perspiration accelerating performance is made with respect to the measurement site with the perspiration acceleration device coupled to the electronic component device, and thereafter, the perspiration acceleration device is replaced with the perspiration collection device with the electronic component device attached to the measurement site, and the perspiration collection and measurement computation performance are made.

7 Claims, 28 Drawing Sheets

(56) References Cited

OTHER PUBLICATIONS

Sugenoya et al., "Device and Method for Accurately Measuring Concentration of Blood Component," U.S. Appl. No. 12/775,646, filed May 7, 2010.

Sugenoya et al., "Device and Method for Accurately Measuring Concentration of Blood Component," U.S. Appl. No. 12/775,648, filed May 7, 2010.

* cited by examiner

DEVICE FOR ACCURATELY MEASURING CONCENTRATION OF COMPONENT IN BLOOD AND CONTROL METHOD OF THE DEVICE

BACKGROUND OF THE INVENTION

1. Field of the Invention

The present invention relates to a device for measuring the concentration of a component in blood and a control method of the device, and in particular, to a device for measuring the concentration of a component in blood using perspiration and a control method of the device.

2. Description of the Related Art

In predetermined diseases such as diabetes, the glucose concentration (hereinafter referred to as blood glucose level) in the blood needs to be measured many times a day. A method of measuring the concentration of a component in the blood such as blood glucose includes a method of analyzing and measuring the collected blood, but because such a method imposes a great burden on the patient, a method that does not involve collecting of blood has been proposed.

A method of measuring the concentration of a component in blood such as blood glucose from the concentration of the component contained in the perspiration is known as the method of measuring without collecting the blood. For instance, U.S. Pat. No. 5,036,861 discloses a method and a device therefor.

In the method disclosed in U.S. Pat. No. 5,036,861, a medical agent is introduced to the measurement site to forcibly cause perspiration, and the perspiration is collected and analyzed to obtain the concentration of the component in the blood. The introduction of the medical agent is a method of subcutaneously impregnating the medical agent to act on the perspiratory gland by attaching to the skin of the patient a patch with a liquid containing a perspiration accelerator, and flowing current to the skin through the patch. In the method of U.S. Pat. No. 5,036,861, the perspiration is absorbed with an absorption pad on the patch after introducing the medical agent to the skin.

However, if the perspiration is collected with the above method, the liquid containing the perspiration accelerator is also absorbed by the absorption pad, and hence there is a problem in that the concentration of the target component in the collected perspiration maybe diluted or false detection may easily occur when detecting the concentration by the sensor.

To solve the above problem, there is proposed a method of once detaching the patch including the liquid containing the perspiration accelerator and cleaning the skin after perspiration, and attaching a pad for collecting perspiration to collect the perspiration. In this case, however, there is a problem in that the perspiration may not be efficiently collected if the position where the patch is attached and the position where the pad is attached are shifted.

SUMMARY OF THE INVENTION

In view of such problems, preferred embodiments of the present invention provide a device for accurately measuring a concentration of a blood component using perspiration and efficiently collecting the perspiration from which the concentration of the blood component can be measured, and a control method of the device.

In accordance with a preferred embodiment of the present invention, a device for measuring a concentration of the blood component includes: a first device including a perspiration accelerating unit arranged to accelerate perspiration from a body surface or a measurement site; a second device including a perspiration collecting unit arranged to collect perspiration from the measurement site; a positioning unit arranged to fix positions of the first device and the second device with respect to the measurement site; and a coupling unit arranged to removably couple the first device or the second device with respect to the positioning unit.

In accordance with another preferred embodiment of the present invention, a control method of a device for measuring a concentration of the blood component which includes a first device including a perspiration accelerating unit arranged to accelerate perspiration from a body surface or a measurement site, a second device including a perspiration collecting unit arranged to collect perspiration from the measurement site and a detector arranged to detect a target component from the perspiration collected by the perspiration collecting unit, and a third device including a positioning unit arranged to fix positions of the first device and the second device with respect to the measurement site, and a coupling unit arranged to removably couple the first device or the second device with respect to the positioning unit, the method including the steps of: determining which of the first device or the second device is coupled to the third device by the coupling unit; controlling the perspiration accelerating performance in the perspiration accelerating unit of the first device when it is determined that the first device is coupled by the coupling unit; controlling detection performance of the target component in the detector of the second device when it is determined that the second device is coupled by the coupling unit; measuring a perspiration concentration of the target component detected by the second device; converting the perspiration concentration of the target component to a blood concentration; and outputting the blood concentration of the target component.

According to various preferred embodiments of the present invention, the perspiration can be efficiently collected, and the concentration of the blood component can be accurately measured using the perspiration.

Other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1A:
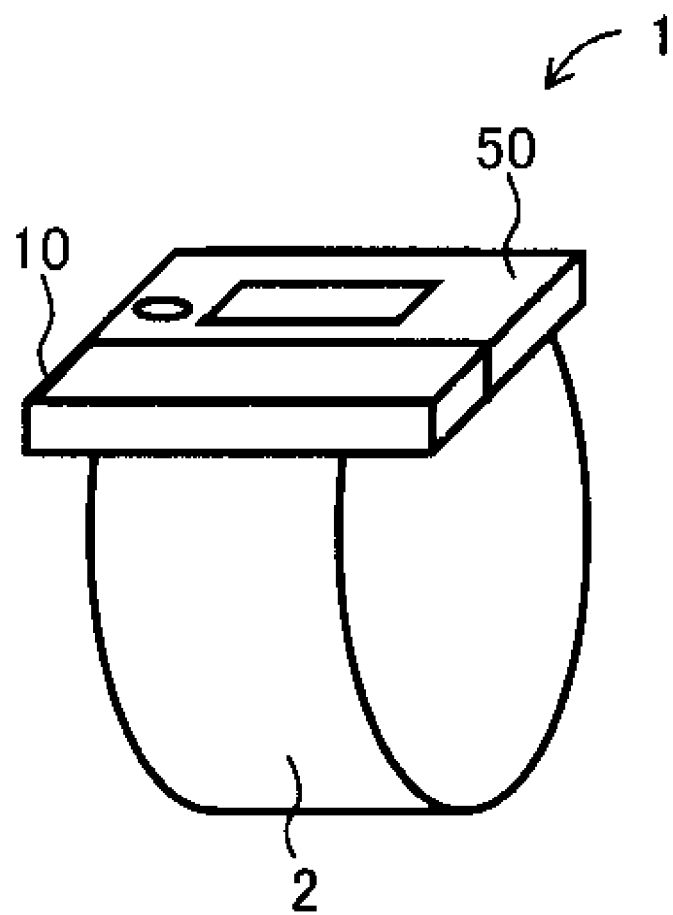
FIG. 1A is a view showing a specific example of an outer appearance of a measurement device according to a preferred embodiment of the present invention, with a perspiration acceleration device coupled to an electronic component device.

Preferred embodiments of the present invention will be hereinafter described with reference to the drawings. In the following description, the same reference numerals are denoted for the same components and the configuring elements. The names and functions thereof are also the same.

Figure 1B:
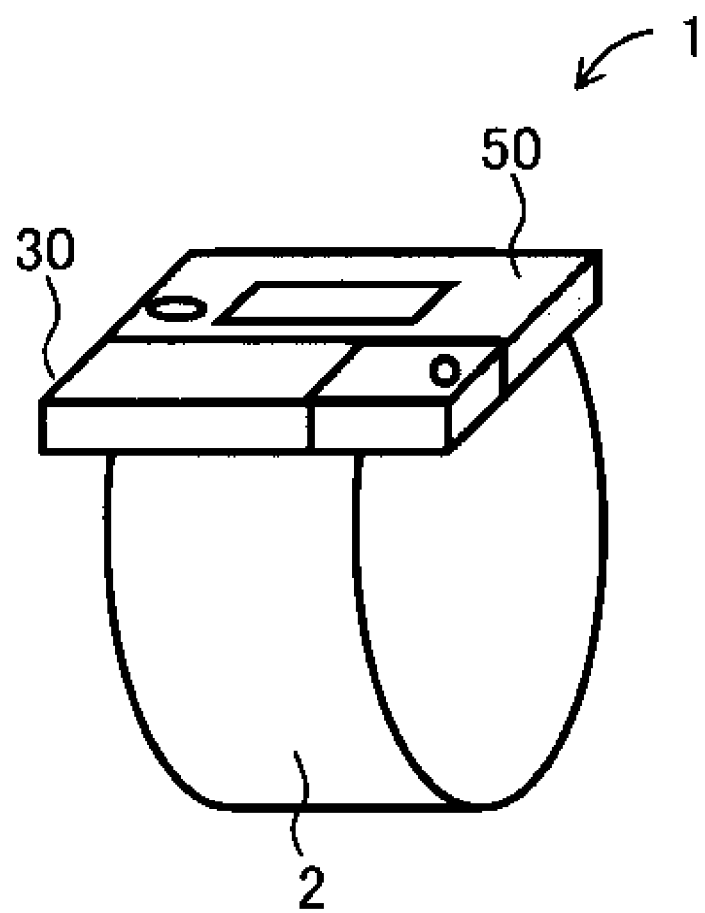
FIG. 1B is a view showing a specific example of an outer appearance of a measurement device according to a preferred embodiment of the present invention, with a perspiration collection device coupled to an electronic component device.
Figure 1C:
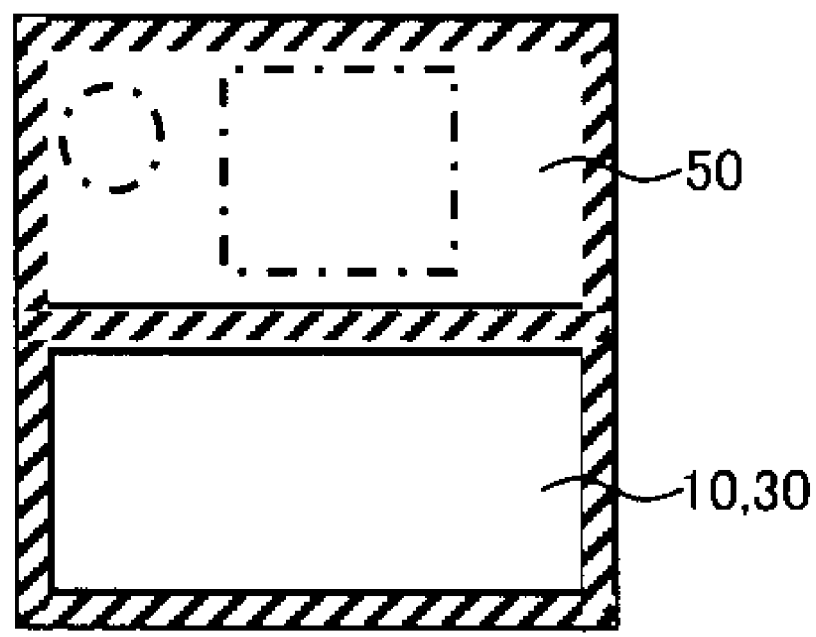
FIG. 1C is a view showing another specific example of an arrangement to fix the measurement device, according to a preferred embodiment of the present invention, to a measurement site.

FIG. 1A and FIG. 1B are views showing a specific example of an outer appearance of a blood component concentration measurement device (hereinafter abbreviated as measurement device) 1 according to the present preferred embodiment. The measurement device 1 includes an electronic component device 50. The electronic component device 50 preferably is removably coupled with a perspiration acceleration device 10 or a perspiration collection device 30 of a body separate from the electronic component device 50. The measurement device 1 has two states including a state (FIG. 1A) in which the perspiration acceleration device 10 is coupled to the electronic component device 50, and a state (FIG. 1B) in which the perspiration collection device 30 is coupled to the electronic component device 50. The measurement device 1 is used by being attached to the measurement site such as a wrist or an ankle with a belt 2 in either of the two states. The belt 2 defines a fixing member arranged to fix the position of the measurement device 1 with respect to the measurement site. The fixing member arranged to fix the position of the measurement device 1 to the measurement site is not limited to the belt, and may be a mechanism, in which an adhesive member (hatching portion of FIG. 1C) is arranged in at least one portion of the measurement device 1, for using the adhesive force, as shown in FIG. 1C.

When the perspiration acceleration device 10 is coupled to the electronic component device 50, the performance of accelerating the perspiration, to be described later, is made in the measurement device 1, and the perspiration from the measurement site is accelerated. Thereafter, the perspiration acceleration device 10 is decoupled from the electronic component device 50 with the measurement device 1 attached to the measurement site with the belt 2, and the perspiration collection device 30 is coupled to the electronic component device 50. When the perspiration collection device 30 is coupled to the electronic component device 50, the perspiration is collected by the perspiration collection device 30, and the detection performance, to be described later, is made.

Figure 2A:
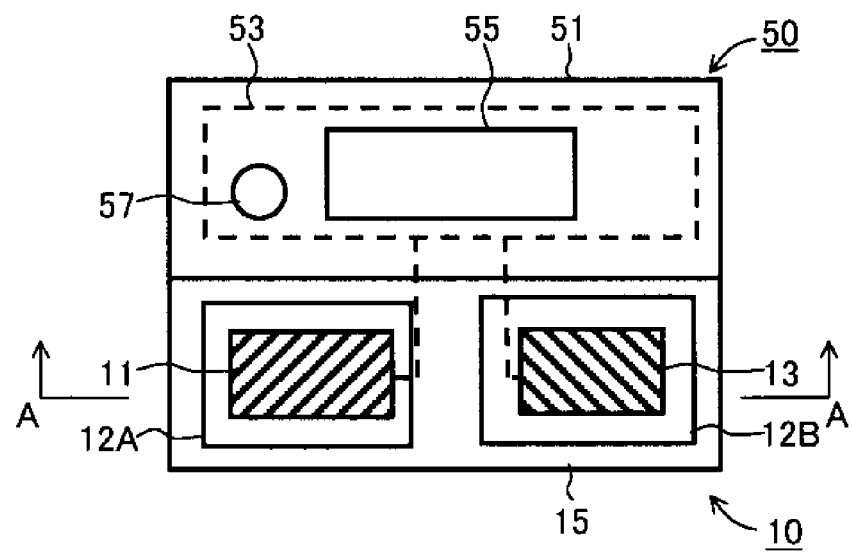
FIG. 2A is a view of the mechanical configuration of the measurement device according to a preferred embodiment of the present invention, with the perspiration acceleration device coupled to the electronic component device, seen from the front surface.

FIG. 2A is a schematic view of the measurement device 1, in which the perspiration acceleration device 10 is coupled to the electronic component device 50, seen from the surface shown on the upper side in FIG. 1A. Hereinafter, the surface shown in FIG. 2A is the front surface. With reference to FIG. 2A, the perspiration acceleration device 10 includes an introducing electrode 11, which is an anode, and a reference electrode 13, which is a cathode, inside a housing 15. The electronic component device 50 includes a control circuit 53 inside the housing 51. The introducing electrode 11 and the reference electrode 13 of the perspiration acceleration device 10 are connected to the control circuit 53 by coupling the perspiration acceleration device 10 to the electronic component device 50. A display 55 is arranged at a position that can be visually recognized when attached to the measurement site using the belt 2 on the housing 51 of the electronic component device 50 such as the surface shown on the upper side in FIG. 1A. The display 55 is also connected to the control circuit 53. An operation button 57 is arranged at the front surface of the housing 51. The operation button 57 is also connected to the control circuit 53.

Figure 2B:
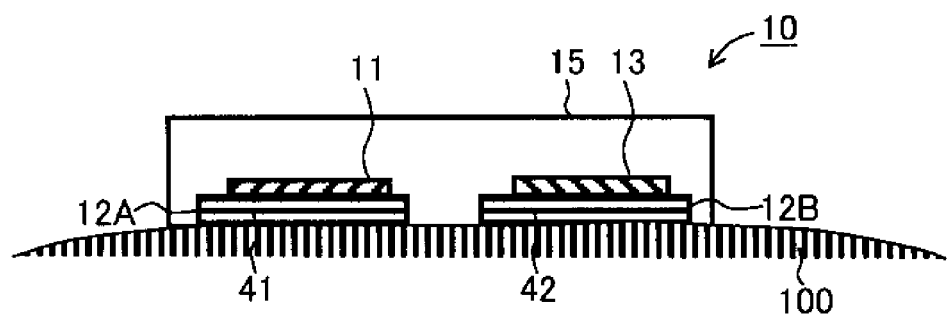
FIG. 2B is a view showing a cross-section at the position shown with an arrow A of FIG. 2A of the mechanical configuration of the measurement device according to a preferred embodiment of the present invention, with the perspiration acceleration device coupled to the electronic component device.

FIG. 2B is a schematic view of a mechanical configuration of the cross-section of the perspiration acceleration device 10 at the position shown with an arrow A in FIG. 2A. With reference to FIG. 2B, the introducing electrode 11 and the reference electrode 13 are arranged at positions close to the surface on the far side from the front surface of the housing 15 in the housing 15, that is, at positions close to the skin 100 or the measurement site when the measurement device 1 is attached to the measurement site using the belt 2. Medical agent regions 12A, 12B are arranged respectively between the introducing electrode 11 and the skin 100 and between the reference electrode 13 and the skin 100, of the housing 15. The medical agent region 12A is preferably set with a member or material such that the perspiration accelerator contacts the skin, such as a sponge 41 including liquid containing medical agent (perspiration accelerator) to accelerate perspiration, such as pilocarpine solution. The medical agent region 12B is preferably set with a buffer, such as a sponge 42 containing buffer solution. The medical agent regions 12A, 12B may have a configuration in which the medical agent is injected as is, a configuration in which the gelatinized medical agent is set, or a configuration in which the medical agent absorbed to absorbent cotton and the like is set. The configurations of the medical agent regions 12A, 12B may be any configuration as long as the medical agents set in the medical agent regions 12A, 12B contact the skin 100 when the perspiration acceleration device 10 is attached to the measurement site.

The control circuit 53 stores a current value in advance. When a control signal to start the perspiration is input from a button 57, the control circuit 53 generates a DC current with a specified current value from the introducing electrode 11 to the reference electrode 13 according to the control signal.

Figure 3A:
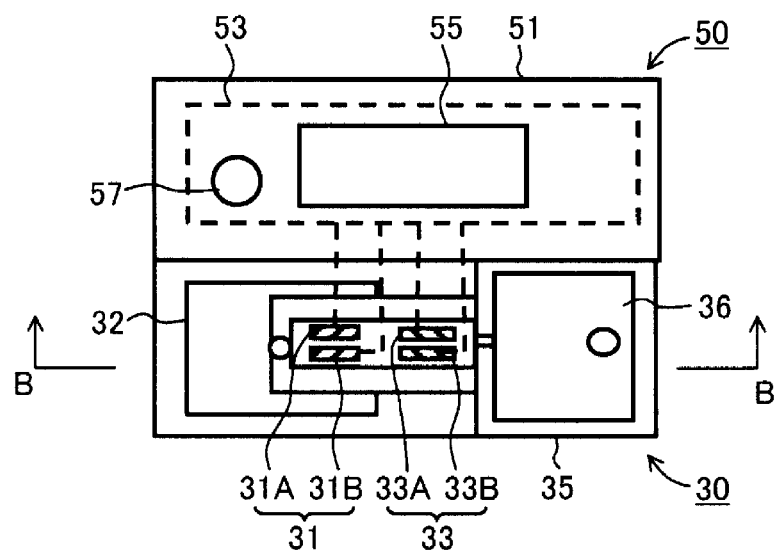
FIG. 3A is a view of the mechanical configuration of the measurement device according to a preferred embodiment of the present invention, with the perspiration collection device coupled to the electronic component device, seen from the front surface.

FIG. 3A is a schematic view of the measurement device 1, with the perspiration collection device 30 coupled to the electronic component device 50, seen from the surface shown on the upper side in FIG. 1B. Hereinafter, the surface shown in FIG. 3A is the front surface. With reference to FIG. 3A, the perspiration collection device 30 includes inside a housing 35 first component detectors 31A, 31B to detect a first component in the perspiration and second component detectors 33A, 33B for detecting a second component. The first component detectors 31A, 31B are representatively referred to as a first component detector 31, and the second component detectors 33A, 33B are representatively referred to as a second component detector 33. The first component detector 31 and the second component detector 33 of the perspiration collection device 30 are connected to the control circuit 53 of the electronic component device 50 by coupling the perspiration collection device 30 to the electronic component device 50.

Figure 3B:
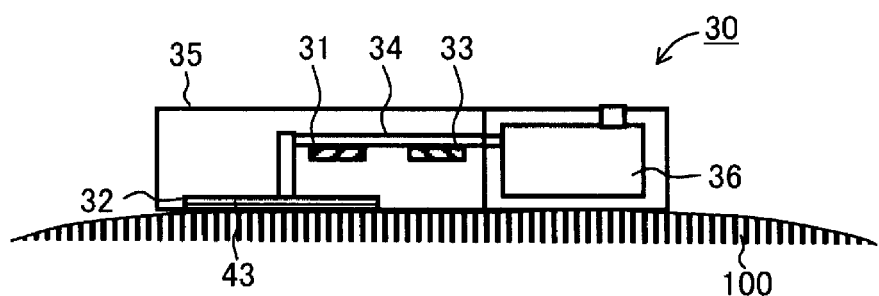
FIG. 3B is a view showing a cross-section at the position shown with an arrow B of FIG. 3A of the mechanical configuration of the measurement device according to a preferred embodiment of the present invention, with the perspiration collection device coupled to the electronic component device.

FIG. 3B is a schematic view of a mechanical configuration of the cross-section of the perspiration collection device 30 at the position shown with an arrow B in FIG. 3A. With reference to FIG. 3B, a perspiration collection region 32 is arranged to define a perspiration collection member at a position close to the surface on the far side from the front surface of the housing 35 in the housing 35, that is, at a position close to the skin 100 or the measurement site when the measurement device 1 is attached to the measurement site using the belt 2, and a member arranged to absorb perspiration from the skin 100, such as a perspiration collection sponge 43, is set. The perspiration collection region 32 may have a configuration to collect perspiration directly from the skin 100, or a configuration in which a medical agent for gelatinizing the perspiration is set. The configuration of the perspiration collection region 32 may be any configuration as long as the perspiration can be collected from the skin 100 when the perspiration collection device 30 is attached to the measurement site. Furthermore, a discarding liquid storage unit 36 arranged to store discarded liquid after component detection, is arranged inside the housing 35 of the perspiration collection device 30, and a conveyance path 34 arranged to convey the perspiration from the perspiration collection region 32 to the discarding liquid storage unit 36 through the first component detector 31 and the second component detector 33 is arranged.

Figure 4:
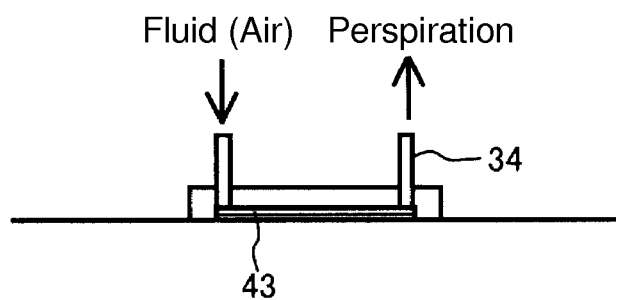
FIG. 4 is a view describing one example of a method of conveying perspiration from a perspiration collection region to a discarding liquid storage unit of the perspiration collection device.

The present invention is not limited to the conveyance path 34 to convey the perspiration as described above, and a method of injecting fluid such as air from one side of the conveyance path 34 including the perspiration collection region 32 and pushing out the internal perspiration to the other side, as shown in FIG. 4, may be adopted.

Figure 5:
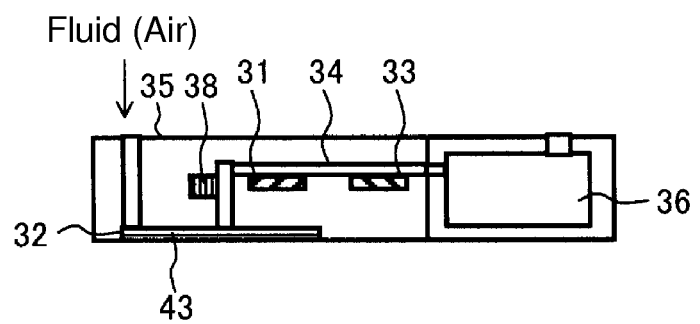
FIG. 5 is a view showing another specific example of the mechanical configuration of the perspiration collection device.

The mechanical configuration shown in FIGS. 2A, 2B and 3A, 3B is a specific example, and the configuration of the perspiration acceleration device 10 and the perspiration collection device 30 is not limited to the illustrated configuration. For instance, as another specific example of the configuration of the perspiration collection device 30, an arrangement shown in FIG. 5 may preferably be provided to convey perspiration in the conveyance path 34. In other words, a liquid sensor 38 arranged to detect a perspiration amount that is collected by the perspiration collection region 32 and that has reached the conveyance path 34 is provided, where the control circuit 53 outputs a control signal to a mechanism injecting a fluid such as compressed air (not shown) to the conveyance path 34 and conveys the perspiration of the perspiration collection region 32 to the first component detector 31 and the second component detector 33, when detecting that the collected perspiration amount reached a predetermined amount based on the detection signal from the liquid sensor 28. Furthermore, the perspiration in the first component detector 31 and the second component detector 33 is conveyed to the discarding liquid storage unit 36 after component detection is performed in the first component detector 31 and the second component detector 33.

First Preferred Embodiment

Figure 6A:
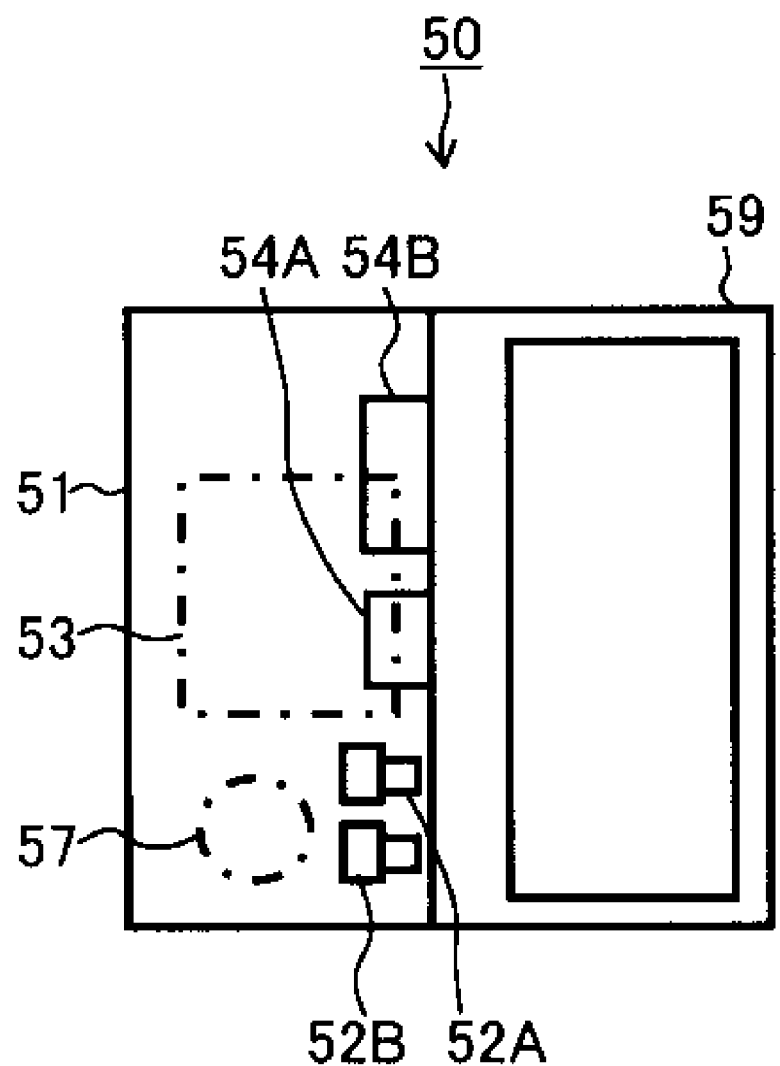
FIG. 6A is a schematic view showing an internal structure when the electronic component device according to a first preferred embodiment of the present invention is seen from the front surface.
Figure 6B:
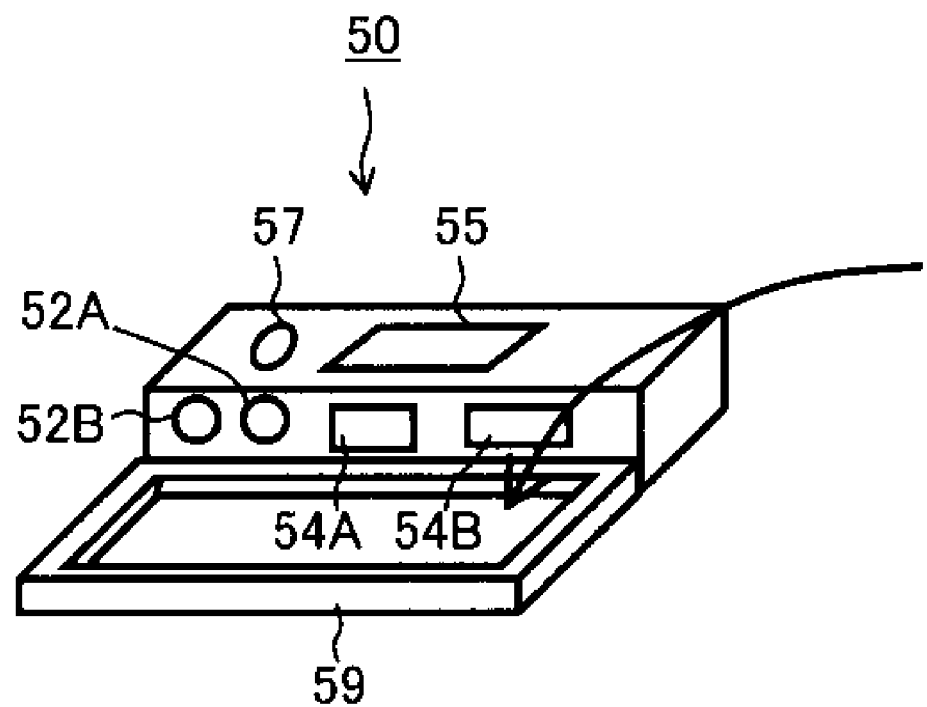
FIG. 6B is a schematic view of the outer appearance when the front surface of the electronic component device according to the first preferred embodiment of the present invention is seen from a diagonal direction.
Figure 6C:
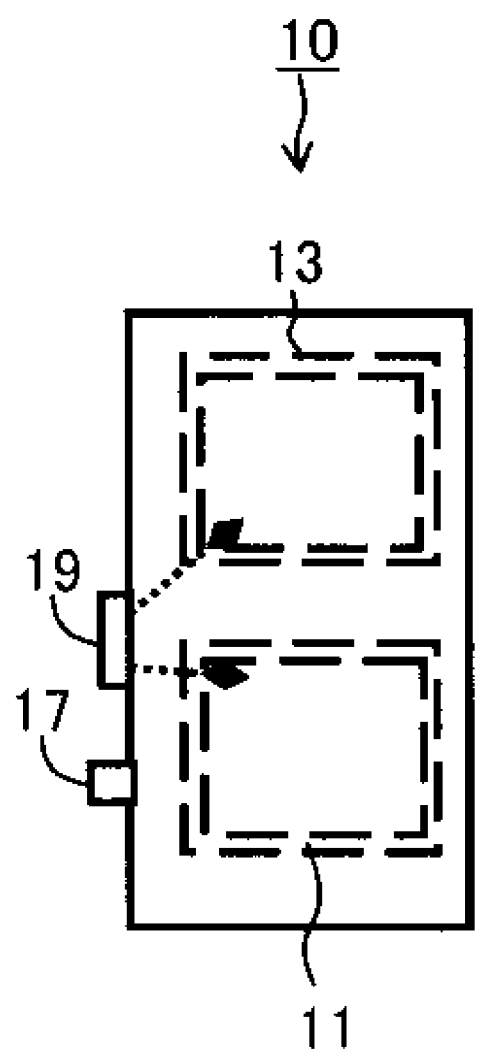
FIG. 6C is a schematic view showing an internal structure when the perspiration acceleration device according to the first preferred embodiment of the present invention is seen from the front surface.
Figure 6D:
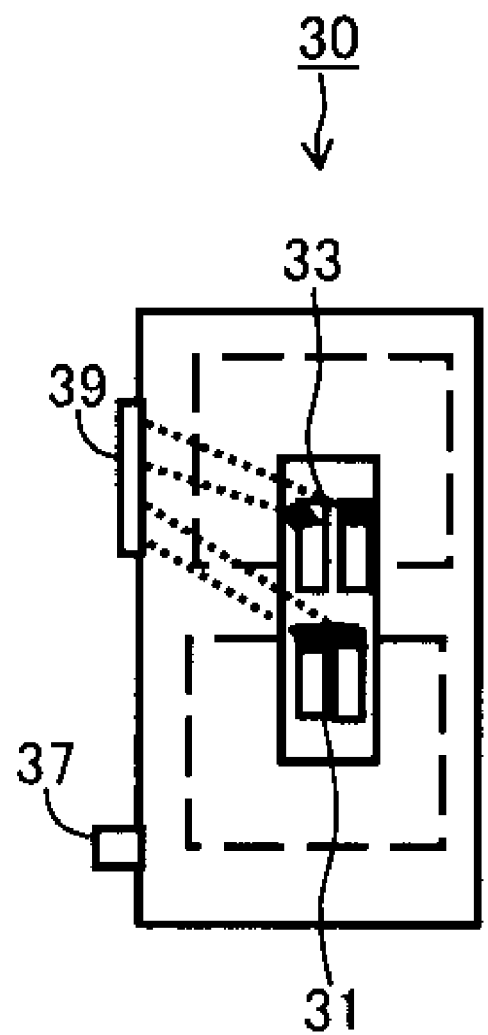
FIG. 6D is a schematic view showing an internal structure when the perspiration collection device according to the first preferred embodiment of the present invention is seen from the front surface.
Figure 6E:
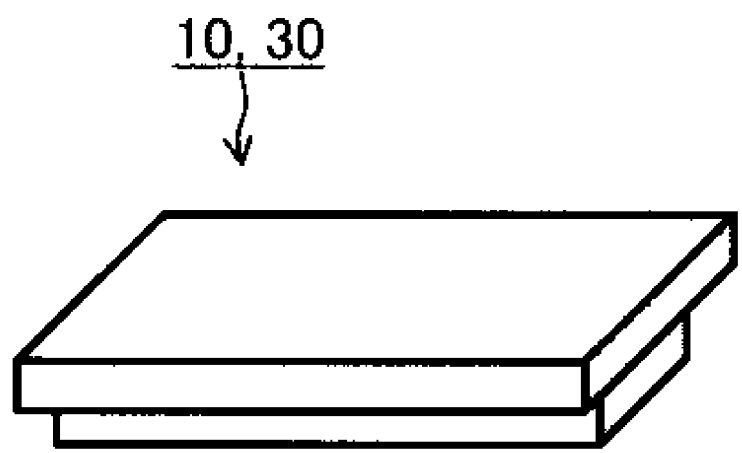
FIG. 6E is a schematic view of the outer appearance when the front surface of the perspiration acceleration device or the perspiration collection device according to the first preferred embodiment of the present invention is seen from a diagonal direction.

FIGS. 6A and 6B are views illustrating the coupling of the electronic component device 50 and the perspiration acceleration device 10, and the coupling of the electronic component device 50 and the perspiration collection device 30 in the first preferred embodiment. FIG. 6A is a schematic view showing an internal structure when the electronic component device 50 is seen from the front surface. FIG. 6B is a schematic view of the outer appearance when the front surface of the electronic component device 50 is seen from a diagonal direction. FIG. 6C is a schematic view of the perspiration acceleration device 10 seen from the front surface. FIG. 6D is a schematic view of the perspiration collection device 30 seen from the front surface. And FIG. 6E is a schematic view of the outer appearance when the front surface of the perspiration acceleration device 10 or the perspiration collection device 30 is seen from a diagonal direction.

Figure 6F:
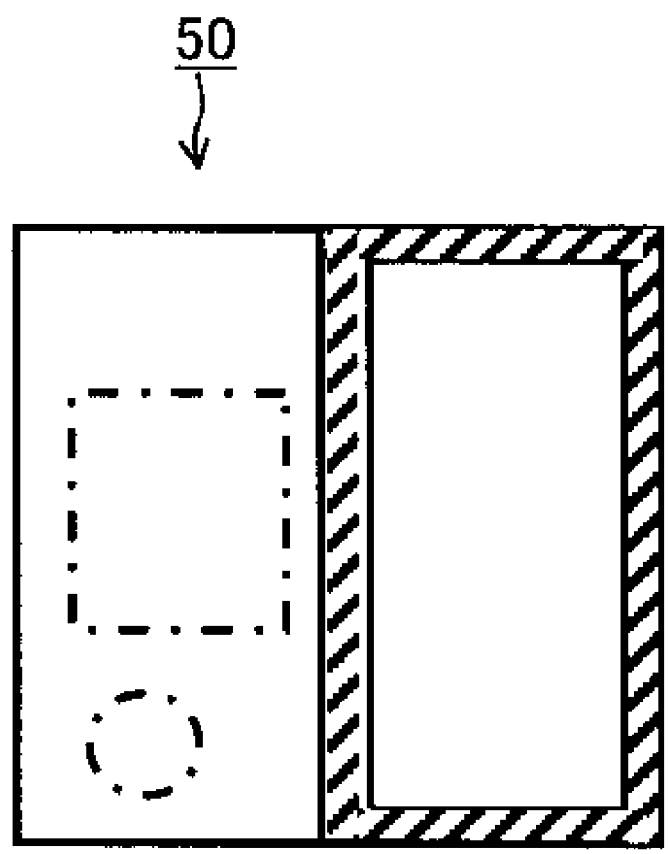
FIG. 6F is a view showing another specific example of an arrangement to couple the perspiration acceleration device or the perspiration collection device to the electronic component device in the first preferred embodiment of the present invention.

With reference to FIG. 6A and FIG. 6B, the electronic component device 50 includes a frame 59 arranged to couple the perspiration acceleration device 10 or the perspiration collection device 30. The frame 59 defines a positioning member arranged to fix the position of the perspiration acceleration device 10 and the perspiration collection device 30 with respect to the measurement site along with the belt 2, and also defines a coupling member with respect to the positioning member. In the present specific example, the perspiration acceleration device 10 or the perspiration collection device 30 is coupled to the electronic component device by fitting the perspiration acceleration device 10 or the perspiration collection device 30 to the frame 59 of the electronic component device 50, as shown with an arrow in FIG. 6B. The frame 59 preferably includes a mechanism arranged to mechanically or electrically fix the fitted perspiration acceleration device 10 or the perspiration collection device 30. The arrangement to couple the perspiration acceleration device 10 or the perspiration collection device 30 to the electronic component device 50 is not limited to the frame. In another example, a mechanism utilizing grooves, concave-convex shapes, and magnetic force formed in the electronic component device 50 and the perspiration acceleration device 10 or the perspiration collection device 30 may be adopted. As shown in FIG. 6F, an adhesive member (hatching portion of FIG. 6F) such as an adhesive tape may be arranged at the periphery of the frame 59, and the adhesive force may be utilized.

With reference to FIG. 6A and FIG. 6B, in the first preferred embodiment, switches 52A, 52B and connectors 54A, 54B are arranged facing the frame 59 in the electronic component device 50. With reference to FIG. 6C, in the first preferred embodiment, a switch 17 is arranged in the perspiration acceleration device 10 at a position corresponding to the switch 52A of the electronic component device 50 when coupled to the electronic component device 50, and a connector 19 is arranged at a position corresponding to the connector 54A of the electronic component device 50. With reference to FIG. 6D, in the first preferred embodiment, a switch 37 is arranged in the perspiration collection device 30 at a position corresponding to the switch 52B of the electronic component device 50 when coupled to the electronic component device 50, and a connector 39 is arranged at a position corresponding to the connector 54B of the electronic component device 50. One of the switch 52A or the switch 17 has a convex shape, and the other has a concave shape, and one of the switch 52B or the switch 37 has a convex shape, and the other has a concave shape. Similarly, one of the connector 54A or the connector 19 has a convex shape, and the other has a concave shape, and one of the connector 54B or the connector 39 has a convex shape, and the other has a concave shape. In the specific examples shown in FIG. 6A to FIG. 6E, the switches 52A, 52B and the connectors 54A, 54B of the electronic component device 50 have a concave shape, and the switch 17 and the connector 19 of the perspiration acceleration device 10 as well as the switch 37 and the connector 39 of the perspiration collection device 30 have a convex shape. Thus, when the perspiration acceleration device 10 is coupled to the electronic component device 50, the switch 52A of the electronic component device 50 is pushed by the switch 17 of the perspiration acceleration device 10 and the connector 54A of the electronic component device 50 is connected to the connector 19 of the perspiration acceleration device 10. When the perspiration collection device 30 is coupled to the electronic component device 50, the switch 52B of the electronic component device 50 is pushed by the switch 37 of the perspiration collection device 30 and the connector 54B of the electronic component device 50 is connected to the connector 39 of the perspiration collection device 30. The connection of the connector 54A and the connector 19 enables a power distribution between the control circuit 53 of the electronic component device 50 and the introducing electrode 11 and the reference electrode 13 of the perspiration acceleration device 10. The connection of the connector 54B and the connector 39 enables a power distribution between the control circuit 53 of the electronic component device 50 and the first component detector 31 and the second component detector 33 of the perspiration collection device 30.

With the measurement device 1 according to the present preferred embodiment having the above configuration, the measurer can release the coupling state of the perspiration acceleration device 10 to the electronic component device 50, with the measurement device 1 attached to the measurement site, and then couple the perspiration collection device 30 to perform the perspiration collection and the measurement computation. Thus, the perspiration is efficiently collected from the same position as the measurement site where the perspiration accelerator is introduced. Since the perspiration acceleration device 10 and the perspiration collection device 30 can be changed, with the electronic component device 50 fixed, the skin of the measurement site can be cleaned and the perspiration accelerator can be prevented from being mixed to the collected perspiration after the perspiration accelerating performance is finished. Furthermore, since the position of the electronic component device 50 is fixed if the measurement device 1 remains attached to the measurement site, even when the coupling state of the perspiration acceleration device 10 or the perspiration collection device 30 is released, the perspiration acceleration device 10 or the perspiration collection device 30 can become the same position with respect to the measurement site when recoupled, such as by replacing the perspiration accelerator during the perspiration accelerating performance.

Figure 7:
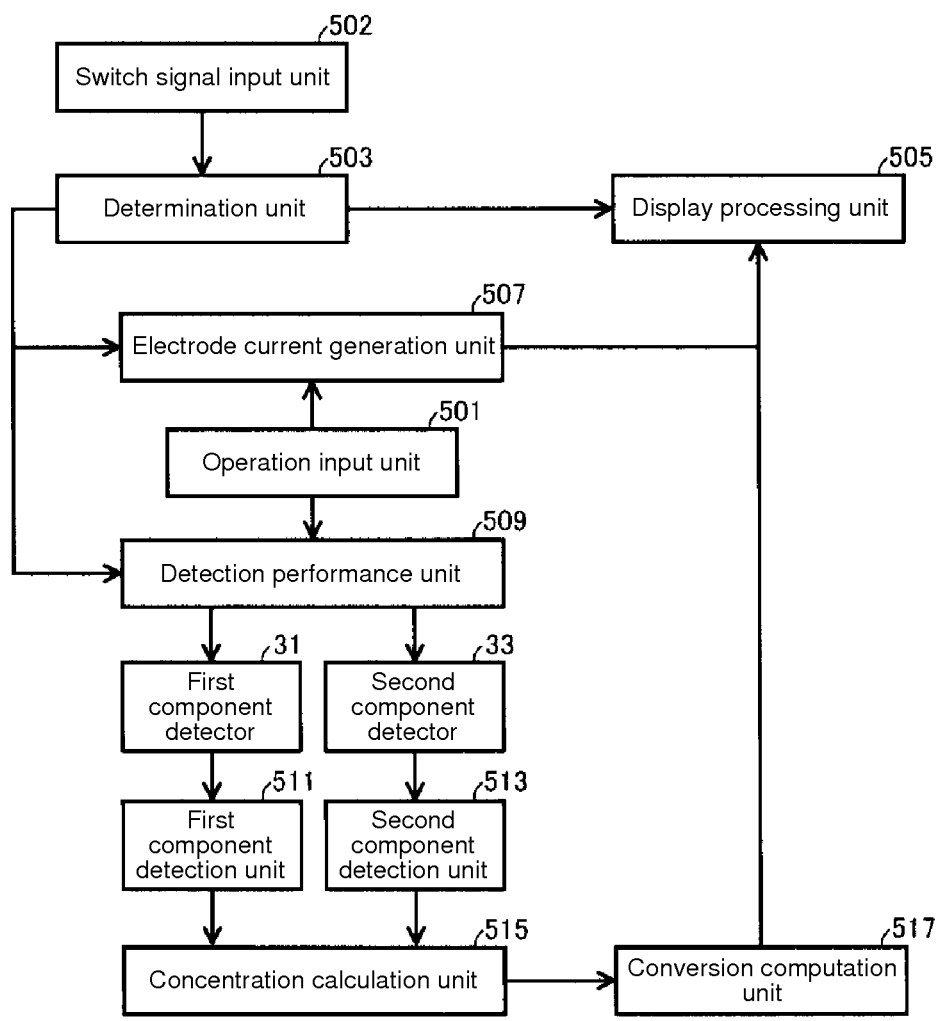
FIG. 7 is a block diagram showing a specific example of a function configuration of the electronic component device according to the first preferred embodiment of the present invention.

FIG. 7 is a block diagram showing a specific example of a functional configuration of the electronic component device 50 for causing perspiration from the skin 100 and collecting the same, and calculating the concentration of the first component in the blood using the concentrations of the first component and the second component in the perspiration, in the measurement device 1 according to the first preferred embodiment. Each function shown in FIG. 7 is a function implemented when the control circuit 53 of the electronic component device 50 executes a predetermined control program, and at least some of the functions may be implemented by the mechanical configuration shown in FIG. 2A, FIG. 3A, and FIG. 6A to FIG. 6D.

With reference to FIG. 7, the function of the electronic component device 50 includes an operation input unit 501 arranged to accept the input of the operation signal from the operation button 57, a switch signal input unit 502 arranged to accept the input of the switch signal from the switches 52A, 52B indicating that the switch 52A or the switch 52B has been pushed, a determination unit 503, a display processing unit 505, an electrode current generation unit 507, a detection performance unit 509, a first component detection unit 511, a second component detection unit 513, a concentration calculation unit 515, and a conversion computation unit 517.

The determination unit 503 is mainly configured by a control circuit 53, and analyzes the content of the signal accepted by the switch signal input unit 502 and determines whether the switch 52A is pushed or the switch 52B is pushed. The determination unit 503 then outputs a signal indicating the determination result to the display processing unit 505. The determination unit 503 outputs a control signal to the electrode current generation unit 507 when the switch 52A is pushed, and outputs a control signal to the detection performance unit 509 when the switch 52B is pushed.

The electrode current generation unit 507 is mainly configured by a control circuit 53, and performs a process of generating a current of a specified value for a predetermined time between the introducing electrode 11 and the reference electrode 13 of the coupled perspiration acceleration device 10 through the connector 54A and the connector 19 according to the control signal from the determination unit 503 and the operation signal from the operation button 57. Through such process, the DC current flows from the introducing electrode 11 towards the reference electrode 13 through the skin 100 via a sponge 41 containing pilocarpine liquid, or liquid containing perspiration accelerator. Thus, the pilocarpine liquid, or the substance of the introducing electrode is subcutaneously impregnated, introduced to act on the perspiratory gland. Such introducing method of the substance is called the iontophoresis method. When a predetermined time elapses from the start of perspiration accelerating performance, the perspiration occurs from the perspiratory gland near the introducing electrode 11. The electrode current generation unit 507 terminates the process of generating current when the predetermined time elapses, and outputs a signal indicating such information to the display processing unit 505.

The detection performance unit 509 is mainly configured by the control circuit 53, and performs a process of a power distribution to the first component detector 31 and the second component detector 33 of the coupled perspiration collection device 30 for a predetermined time through the connector 54B and the connector 39, according to the control signal from the determination unit 503 and the operation signal from the operation button 57 to achieve a state in which the first component and the second component in the perspiration can be detected.

The first component detector 31 and the second component detector 33 of the perspiration collection device 30 have a configuration of detecting the component in the perspiration, and are not limited to a specific configuration. For instance, a configuration of detecting the component by measuring the wavelength of the radiation light may be adopted, or a configuration of using an enzyme electrode method may be adopted. A configuration according to the first component and the second component to be measured may also be adopted. With the first component detector 31 and the second component detector 33 as configurations using the enzyme electrode method, the perspiration collection device 30 can be miniaturized compared to other configurations such as the configuration of measuring the wavelength of the radiation light.

The first component is a component to be subjected to a calculation of the blood concentration, and corresponds to a component in which relevance is found between the change in concentration in the perspiration and the change in concentration in the blood. Specifically, a sugar (glucose) corresponds to such a component, and the first component is assumed as a sugar in this specific example.

The second component is a component in the perspiration other than the first component, and preferably corresponds to a component in which relevance is not found between the change in concentration in the perspiration and the change in concentration of the first component in the blood, or in which the relevance is lower than a predetermined correlation coefficient. If the first component is a sugar, the second component includes, in addition to glutamic acid, for example, other amino acids such as lysine, glutamine, and asparagine acid, calcium, and kalium, where the second component is assumed as glutamic acid in this specific example.

The first component detector 31 of the perspiration collection device 30 has a configuration in which glucose oxidase and an electrode are combined using an enzyme electrode method to detect the sugar as the first component. The second component detector 33 has a configuration in which L-glutamate oxidase and an electrode are combined using an enzyme electrode method to detect the glutamic acid as the second component.

Through the process of the detection performance unit 509 of the electronic component device 50, the first component detector 31 and the second component detector 33 of the perspiration collection device 30 detect the first component and the second component in the perspiration conveyed from the perspiration collection region 32 to the discarding liquid storage unit 36 for a predetermined time, and output a signal indicating the same.

A first component detection unit 511 and a second component detection unit 513 are mainly configured by a control circuit 53, and receive the signal from the first component detector 31 and the second component detector 33 of the perspiration collection device 30 through the connector 54B and the connector 39, respectively, and output a detection signal corresponding to the detection amount to the concentration calculation unit 515.

The concentration calculation unit 515 is mainly configured by the control circuit 53, and calculates the concentration of the first component in the perspiration based on the detection signal input from the first component detection unit 511 according to a predetermined computation program. Similarly, the concentration calculation unit 515 calculates the concentration of the second component in the perspiration based on the detection signal input from the second component detection unit 513. The signal indicating the calculated concentration is input to the conversion computation unit 517.

The conversion computation unit 517 is mainly configured by the control circuit 53, and performs a computation to convert the concentration of the first component in the perspiration to the concentration of the first component in the blood using the concentration of the first component and the concentration of the second component in the perspiration according to a predetermined computation program, and outputs a signal indicating the computation result to the display processing unit 505. The specific computation method in the conversion computation unit 517 is not limited to a specific computation method in the present invention.

The display processing unit 505 performs a display process to display on the display 55 based on the signal from the determination unit 503, the signal from the electrode current generation unit 507, and the signal from the conversion computation unit 517. The coupling of the perspiration acceleration device 10 or the perspiration collection device 30 to the electronic component device 50 is displayed on the display 55 by performing the display process based on the signal from the determination unit 503. The termination of the perspiration accelerating performance in the perspiration acceleration device 10 is displayed on the display 55 by performing the display process based on the signal from the electrode current generation unit 507. The concentration of the first component in the blood is displayed on the display 55 as a computation result by performing the display process based on the signal from the conversion computation unit 517.

Figure 8:
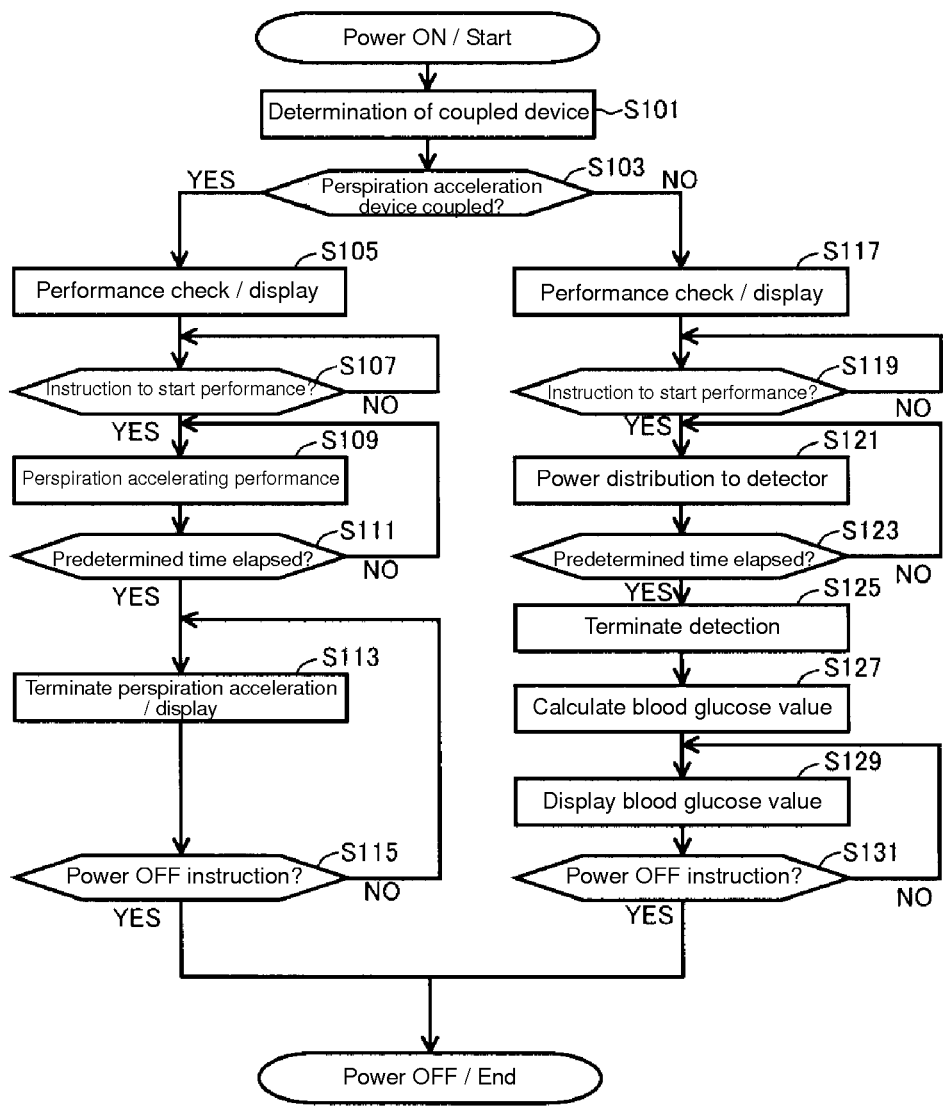
FIG. 8 is a flowchart showing the flow of processes in the electronic component device according to the first preferred embodiment of the present invention.

FIG. 8 is a flowchart showing the flow of processes in the electronic component device 50 for causing perspiration from the skin and collecting the same and calculating the concentration of the first component in the blood using the concentrations of the first component and the second component in the perspiration in the measurement device 1 according to the first preferred embodiment. The processes shown in the flowchart of FIG. 8 are implemented when the control circuit 53 executes a predetermined computation program, and controls each unit shown in FIG. 2A, FIG. 3A, and FIG. 6A to FIG. 6D to exhibit the functions shown in FIG. 7. The processes shown in FIG. 8 are processes executed when the perspiration acceleration device 10 or the perspiration collection device 30 is coupled to the electronic component device 50, and the operation of power ON is performed with the operation button 57, etc.

With reference to FIG. 8, first, whether the switch 52A is pushed or the switch 52B is pushed is determined based on the switch signal from the switch signal input unit 502 in the determination unit 503, so that either of the perspiration acceleration device 10 or the perspiration collection device 30 is coupled to the electronic component device 50 is determined (step S101).

If the perspiration acceleration device 10 is coupled (YES in step S103), the perspiration accelerating performance after step S105 is made. The perspiration accelerating performance after step S105 starts when the measurer attaches the sponge 41 with liquid containing perspiration accelerator such as pilocarpine solution to the medical agent region 12A, attaches the introducing electrode 11 so as to contact the sponge 41, then attaches the measurement device 1, with the perspiration acceleration device 10 coupled to the electronic component device 50, to the measurement site using the belt 2 so that the sponge 41 contacts the skin 100, and then performs the operation of the power ON with the operation button 57, and the like.

When the perspiration accelerating performance starts, the current generation performance is first checked by the electrode current generation unit 507, etc., the perspiration acceleration device 10 is connected to the display 55 by the display process in the display processing unit 505, and then a display indicating the state the perspiration acceleration performance can be made is displayed (step S105).

Thereafter, when accepting an input of the operation signal instructing the start of the performance from the operation button 57 at the operation input unit 501 (YES in step S107), the process of generating the current for flowing a predetermined DC current from the introducing electrode 11 to the reference electrode 13 is executed and the perspiration accelerating performance is made in the electrode current generation unit 507 (step S109). The perspiration accelerating performance is made for a predetermined time, and after the predetermined time has elapsed (YES in step S111), the electrode current generation unit 507 terminates the perspiration accelerating performance by terminating the process of generating the current, and a display indicating that the perspiration accelerating performance is terminated is made on the display 55 by the display process in the display processing unit 505 (step S113). A series of processes is terminated when accepting the input of the operation signal for instructing power OFF from the operation button 57 thereafter at the operation input unit 501 (YES in step S115).

If the perspiration collection device 30 is coupled (NO in step S103), the perspiration collection and the measurement computation performance after step S117 are made. The perspiration collection and the measurement computation performance after step S117 start after the perspiration accelerating performance is terminated when the measurer decouples the perspiration acceleration device 10 from the electronic component device 50 and couples the perspiration collection device 30 with the measurement device 1 attached, and performs the operation of power ON with the operation button 57 and the like. In this case, the perspiration perspired from the skin 100 where the pilocarpine solution is impregnated is collected by the sponge 43 of the perspiration collection region 32 of the perspiration collection device 30.

When the perspiration collection and the measurement computation performance start, the detection occurrence performance is first checked by the detection performance unit 509 and the like, and then the display indicating that the perspiration collection device 30 is coupled and that the state of performing the perspiration collection and the measurement computation is obtained is made on the display 55 by the display process in the display processing unit 505 (step S117).

Thereafter, when accepting the input of the operation signal instructing the start of the performance from the operation button 57 at the operation input unit 501 (YES in step S119), the process of a power distribution to the first component detector 31 and the second component detector 33, and detecting the first component and the second component in the first component detection unit 511 and the second component detection unit 513 is executed in the detection performance unit 509 (step S121). The power distribution to the first component detector 31 and the second component detector 33 is performed for a predetermined time. After a predetermined time has elapsed (YES in step S123), the detection performance unit 509 terminates the process of detecting the first component and the second component by terminating the process of the power distribution (step S125). Subsequently, the concentration in the perspiration of the first component and the concentration in the perspiration of the second component are calculated in the concentration calculation unit 515, the process of converting the concentration in the perspiration of the first component to the blood concentration based on the above concentrations in the perspiration is performed in the conversion computation unit 517, and the blood glucose level, or the blood concentration of the first component is calculated (step S127). Furthermore, a display indicating the blood glucose level calculated in step S127 is made on the display 55 by the display process in the display processing unit 505 (step S129). A series of processes is terminated when accepting the input of the operation signal for instructing power OFF from the operation button 57 thereafter at the operation input unit 501 (YES in step S131).

The control circuit 53 of the electronic component device 50 has a memory function, and when the perspiration accelerating performance after step S105 is terminated, stores an indication thereof, and determines that the perspiration collection device 30 is coupled in the determination of step S101 thereafter. In this case, if again it is determined that the perspiration acceleration device 10 is coupled in the determination of step S101 after the termination of the perspiration accelerating performance, an error may be displayed on the display 55. With such a configuration, the perspiration accelerating performance is not re-performed even if the perspiration acceleration device 10 is again coupled by mistake instead of the perspiration collection device 30 after the perspiration acceleration device 10 is coupled to the electronic component device 10 and the perspiration accelerating performance is made, and the notification thereof can be provided.

The control circuit 53 of the electronic component device 50 has a timer function, and the error may be displayed on the display 55 if it is not determined that the perspiration collection device 30 is coupled in the determination of step S101 within a predetermined time after the start of the perspiration accelerating performance in step S109 or after the termination of the perspiration accelerating performance in step S113. With such a configuration, notification that the collection of the perspiration is difficult may be informed when the perspiration collection device 30 is coupled after a time, in which the perspiration can be collected, has elapsed after the perspiration accelerating performance.

The method of coupling the perspiration acceleration device 10 to the electronic component device 50, the method of coupling the perspiration collection device 30 to the electronic component device 50, and the method of determining which device is coupled to the electronic component device 50 shown in the first preferred embodiment are specific examples, and are not limited to the above methods. The other methods are described as the second preferred embodiment and the third preferred embodiment.

Second Preferred Embodiment

Figure 9A:
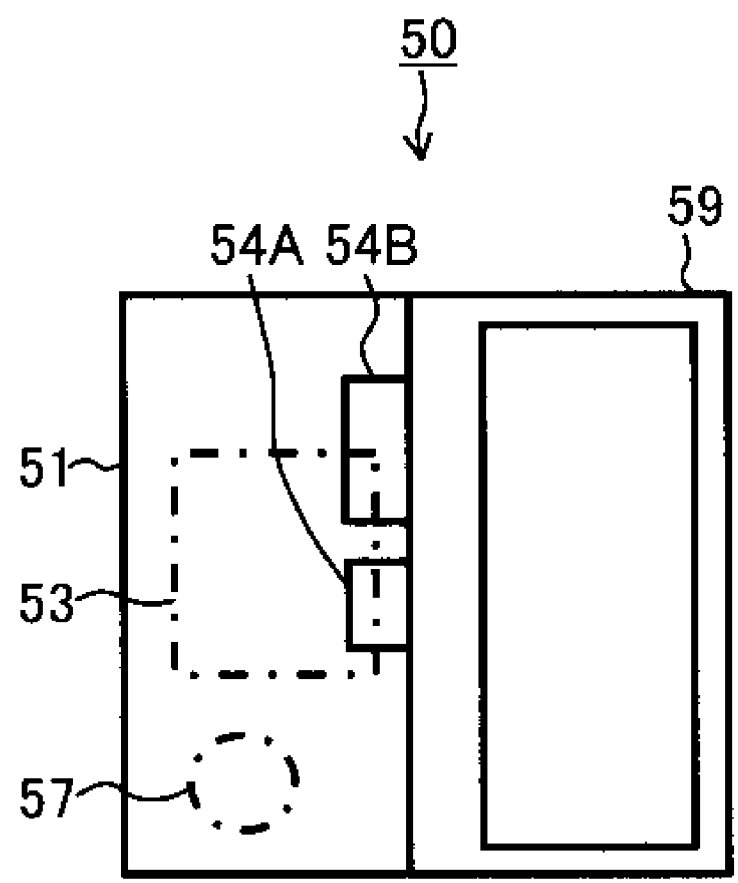
FIG. 9A is a view showing a specific example of the configuration of the electronic component device according to a second preferred embodiment of the present invention.
Figure 9B:
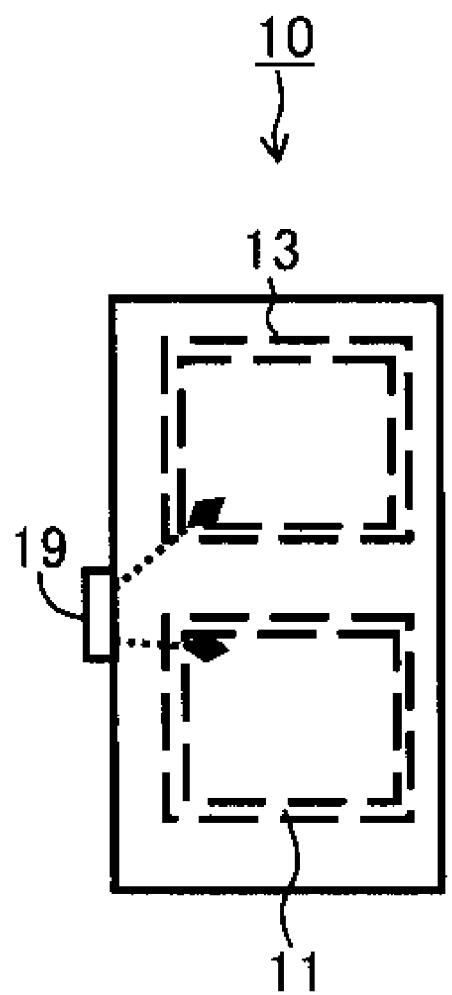
FIG. 9B is a view showing a specific example of the configuration of the perspiration acceleration device according to the second preferred embodiment of the present invention.
Figure 9C:
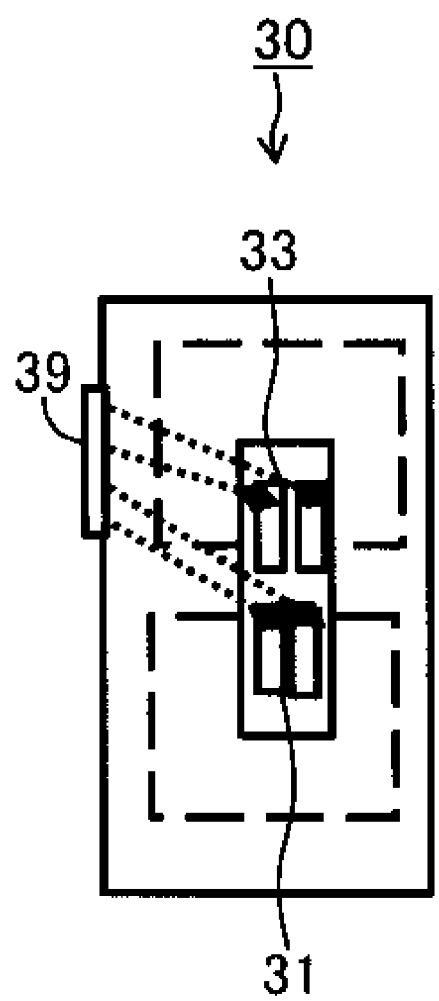
FIG. 9C is a view showing a specific example of the configuration of the perspiration collection device according to the second preferred embodiment of the present invention.

As the second preferred embodiment, FIG. 9A to FIG. 9C each shows another configuration example of the electronic component device 50, the perspiration acceleration device 10, and the perspiration collection device 30. In the configurations shown in FIG. 9A to FIG. 9C, the switches 52A, 52B, the switch 17, and the switch 37 are not arranged in the electronic component device 50, the perspiration acceleration device 10, and the perspiration collection device 30 of the configurations according to the first preferred embodiment shown in FIG. 6A to FIG. 6E.

In the second preferred embodiment, the connectors 54A, 54B of the electronic component device 50 have functions similar to the switches 52A, 52B according to the first preferred embodiment. In other words, the determination unit 503 of the electronic component device 50 according to the second preferred embodiment determines which of the perspiration acceleration device 10 or the perspiration collection device 30 is coupled to the electronic component device 50 by detecting which connectors 54A or 54B, is conducted when a power is distributed to the electrode current generation unit 507 and the detection performance unit 509 in step S101.

Third Preferred Embodiment

Figure 10A:
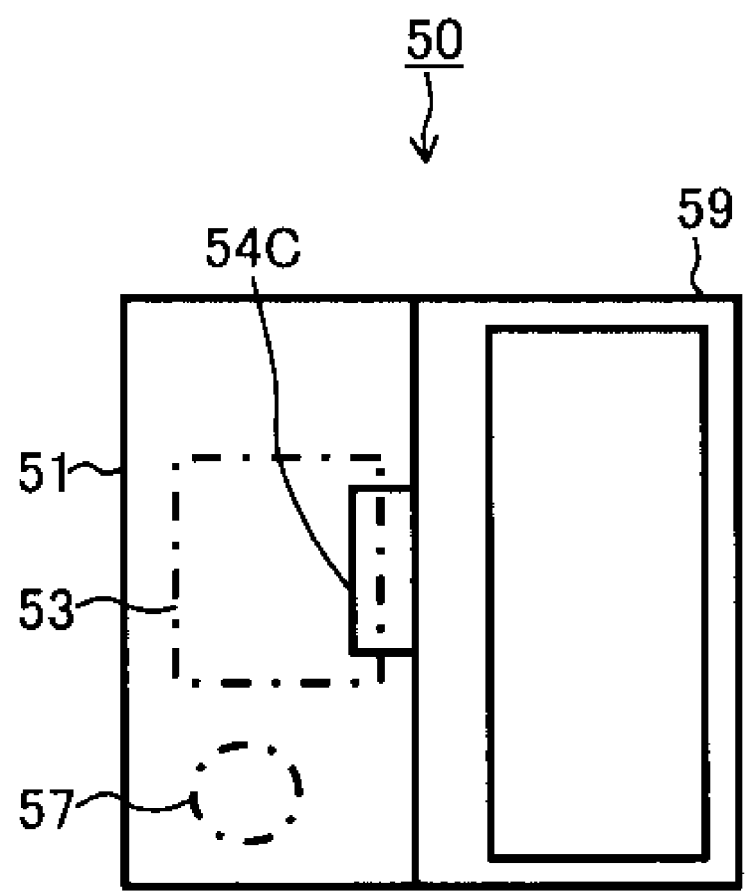
FIG. 10A is a view showing a specific example of the configuration of the electronic component device according to a third preferred embodiment of the present invention.
Figure 10B:
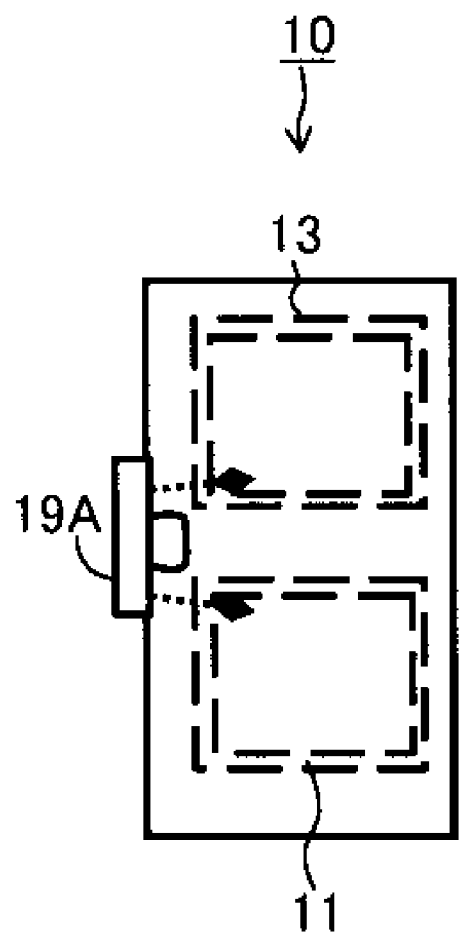
FIG. 10B is a view showing a specific example of the configuration of the perspiration acceleration device according to the third preferred embodiment of the present invention.
Figure 10C:
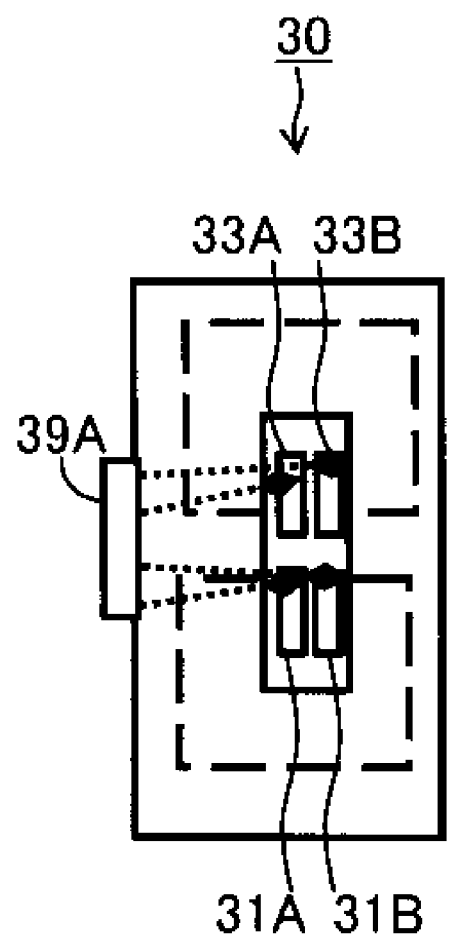
FIG. 10C is a view showing a specific example of the configuration of the perspiration collection device according to the third preferred embodiment of the present invention.

As the third preferred embodiment, FIG. 10A to FIG. 10C each shows another configuration example of the electronic component device 50, the perspiration acceleration device 10, and the perspiration collection device 30. Each configuration shown in FIG. 10A to FIG. 10C is a configuration in which only one connector is arranged in the electronic component device 50, of the configuration according to the second preferred embodiment shown in FIG. 9A to FIG. 9C. With reference to FIG. 10A to FIG. 10C, the electronic component device 50 according to the third preferred embodiment includes one connector 54C in place of the connectors 54A, 54B, the perspiration acceleration device 10 includes a connector 19A in place of the connector 19, and the perspiration collection device 30 includes a connector 39A in place of the connector 39.

The connector 54C, the connector 19A, and the connector 39A each includes a number of terminals corresponding to that of the first component detector 31 and the second component detector 33 of the perspiration collection device 30. In this specific example, the perspiration collection device 30 includes the first component detectors 31A, 31B and the second component detectors 33A, 33B, and thus the connector 54C, the connector 19A, and the connector 39A are connectors of four-terminals.

In the perspiration acceleration device 10, the first terminal and the fourth terminal of the connector 19A are connected to the introducing electrode 11 and the reference electrode 13, and the second terminal and the third terminal are short circuited. In the perspiration collection device 30, the first terminal to the fourth terminal of the connector 39A are respectively connected to the first component detectors 31A, 31B and the second component detectors 33A, 33B.

The determination unit 503 of the electronic component device 50 according to the third preferred embodiment determines that the perspiration acceleration device 10 is coupled to the electronic component device 50 by detecting which terminal of the first terminal to the fourth terminal of the connector 54C is conducted when a power is distributed to the electrode current generation unit 507 and the detection performance unit 509 in step S101, and detecting that the connected second terminal and the third terminal are short circuit. If not, determination is made that the perspiration collection device 30 is coupled.

The configuration of the electronic component device 50, the perspiration acceleration device 10, and the perspiration collection device 30 can be simplified by configuring the configuration of the measurement device 1 as in the configuration of the second preferred embodiment or the configuration of the third preferred embodiment, which contributes to miniaturization, lower weight, and lower cost.

Fourth Preferred Embodiment

In the first preferred embodiment to the third preferred embodiment, the electronic component device 50 includes the control circuit 53, the display 55, the operation button 57, and the like, and the configuration of the perspiration acceleration device 10 or the perspiration collection device 30 is connected to the control circuit 53 by coupling the perspiration acceleration device 10 or the perspiration collection device 30 to the electronic component device 50, but the configuration is not limited regarding which device includes each configuration of the measurement device 1. As a fourth preferred embodiment, FIG. 11 shows a configuration example in which each of the perspiration acceleration device 10 and the perspiration collection device 30 includes the configuration of the control circuit 53, the display 55, the operation button 57 and the like of the electronic component device 50, and only the frame 59, or the positioning member is attached to the measurement site with the belt 2 in place of the electronic component device 50.

Figure 11:
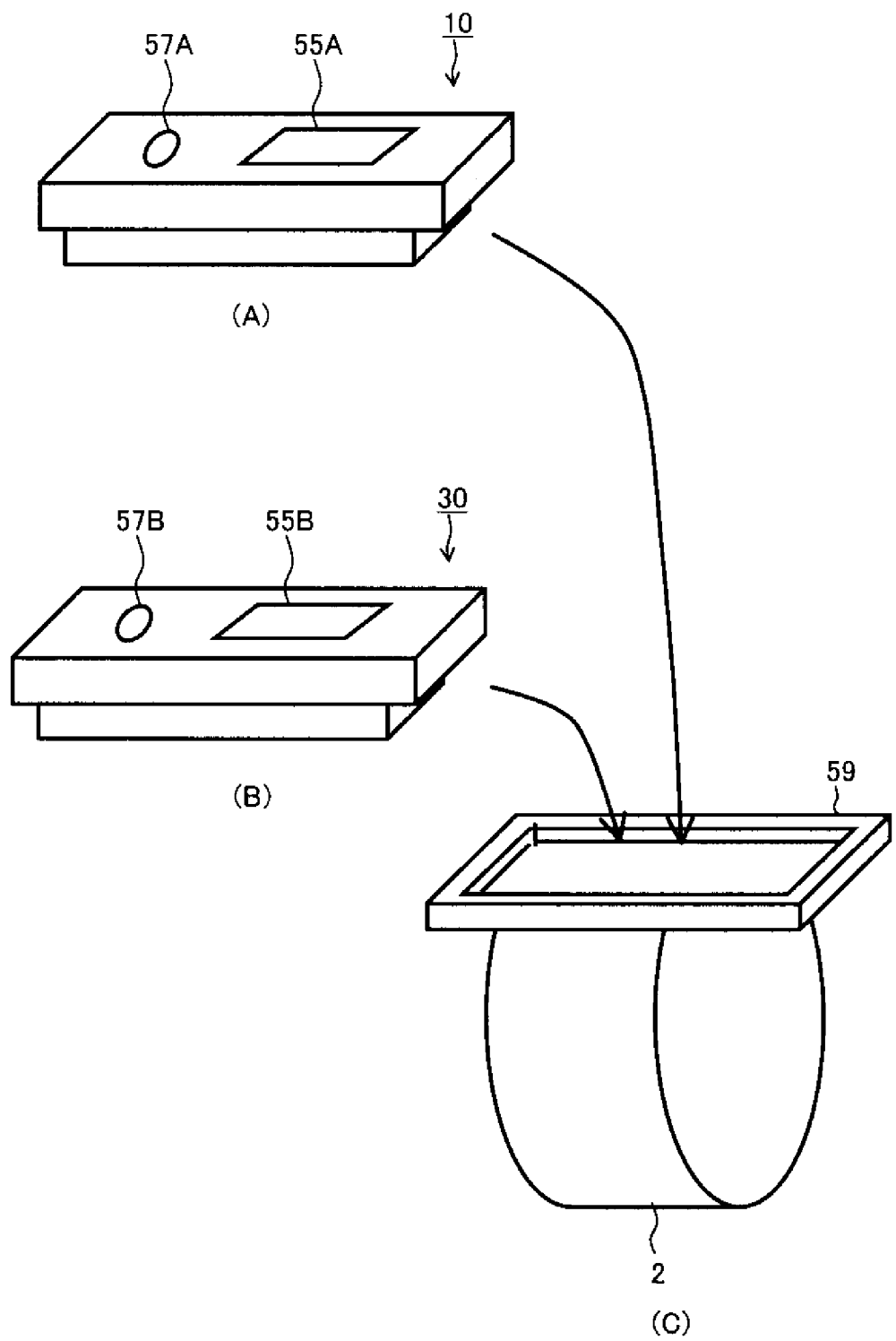
FIG. 11 is a view showing a specific example of a configuration of the measurement device 1 according to a fourth preferred embodiment of the present invention.

With reference to the (A) portion and the (B) portion of the FIG. 11, the perspiration acceleration device 10 and the perspiration collection device 30 according to the fourth preferred embodiment includes the display 55A and the operation button 57A, and the display 55B and the operation button 57B, respectively. The devices also include the control circuit (not shown). Therefore, in the fourth preferred embodiment, the perspiration acceleration device 10 and the perspiration collection device 30 respectively include the configuration contained in the housing 51 of the electronic component device 50 shown in the first preferred embodiment to the third preferred embodiment. In the fourth preferred embodiment, with reference to the (C) portion of FIG. 11, only the frame 59, which is the coupling member or the positioning member, is fixed to the measurement site with the belt 2 in place of the electronic component device 50, and the perspiration acceleration device 10 or the perspiration collection device 30 is coupled to the frame 59.

In the control circuit of the perspiration acceleration device 10 and the control circuit of the perspiration collection device 30, the perspiration acceleration performance after step S105 and the perspiration collection and measurement computation performance after step S117 are executed, respectively. The respective performance is made in each control circuit when the perspiration acceleration device 10 or the perspiration collection device 30 is coupled to the frame 59, and the operation button 57A or the operation button 57B is operated.

With the measurement device 1 according to the fourth preferred embodiment having the above configuration, the perspiration is efficiently collected from the same position as the measurement site where the perspiration accelerator is introduced. The configuration of electrically connecting the electronic component device 50 and the perspiration acceleration device 10, as well as the electronic component device 50 and the perspiration collection device 30, and the configuration of determining which device is coupled to the electronic component device 50, which were necessary in the first preferred embodiment to the third preferred embodiment, may become unnecessary, and the configuration and the process can be facilitated.

Fifth Preferred Embodiment

In the first preferred embodiment to the fourth preferred embodiment, the perspiration acceleration device 10 and the perspiration collection device 30 are configured by different devices, but the perspiration acceleration device 10 and the perspiration collection device 30 may be configured by a perspiration acceleration/perspiration collection device 70A, which is one device including a perspiration accelerating unit 10A and a perspiration collecting unit 30A, and the perspiration acceleration/perspiration collection device 70A may function as the perspiration acceleration device 10 or the perspiration collection device 30 depending on the coupling form with respect to the electronic component device 50. As a fifth preferred embodiment, FIG. 12A to FIG. 12D shows an example in which the measurement device 1 is configured by the electronic component device 50 and the perspiration acceleration/perspiration collection device 70A.

Figure 12A:
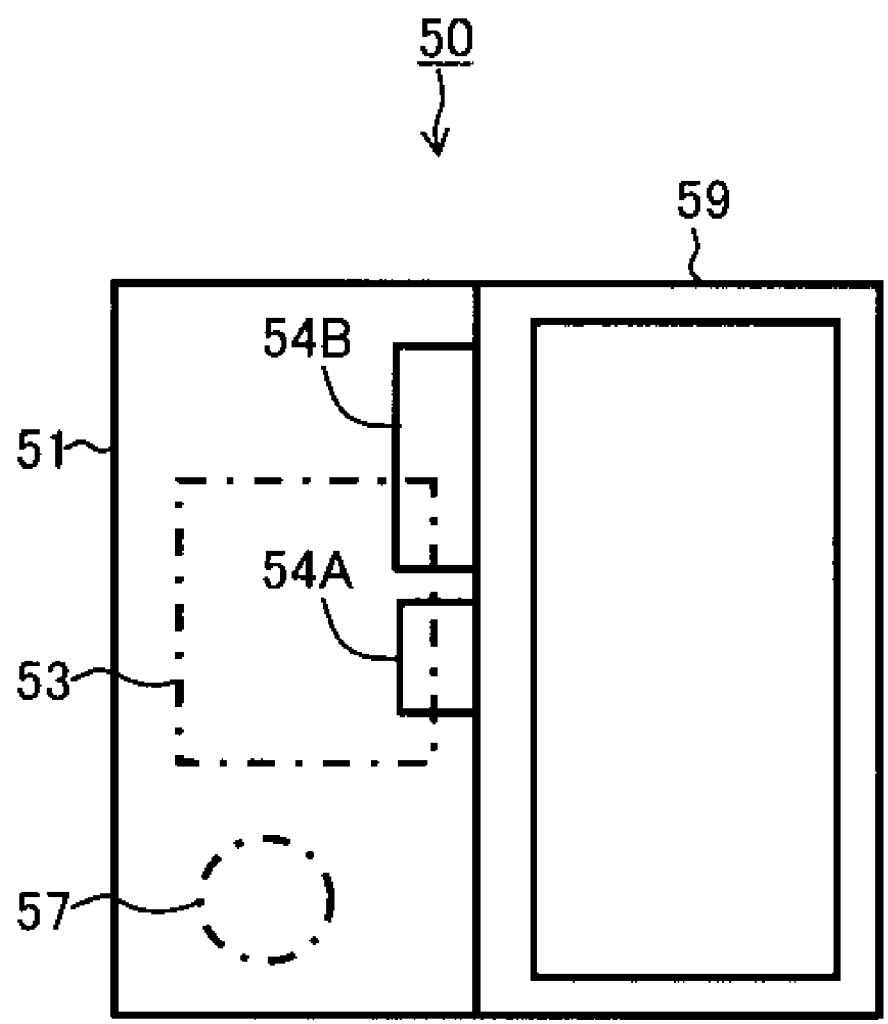
FIG. 12A is a schematic view showing an internal structure when the electronic component device according to a fifth preferred embodiment of the present invention is seen from the front surface.
Figure 12B:
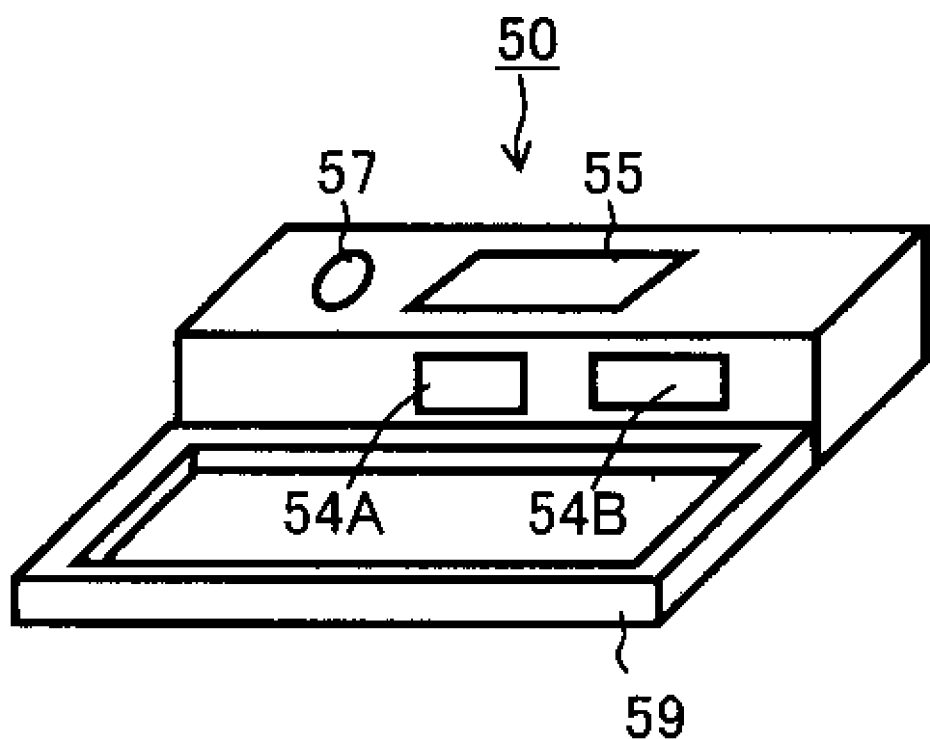
FIG. 12B is a schematic view of an outer appearance when the front surface of the electronic component device according to the fifth preferred embodiment of the present invention is seen from a diagonal direction.

With reference to FIG. 12A and FIG. 12B, the configuration of the electronic component device 50 according to the fifth preferred embodiment is similar to the configuration of the electronic component device 50 according to the second preferred embodiment shown in FIG. 9A, and the electronic component device 50 includes connectors 54A, 54B.

Figure 12C:
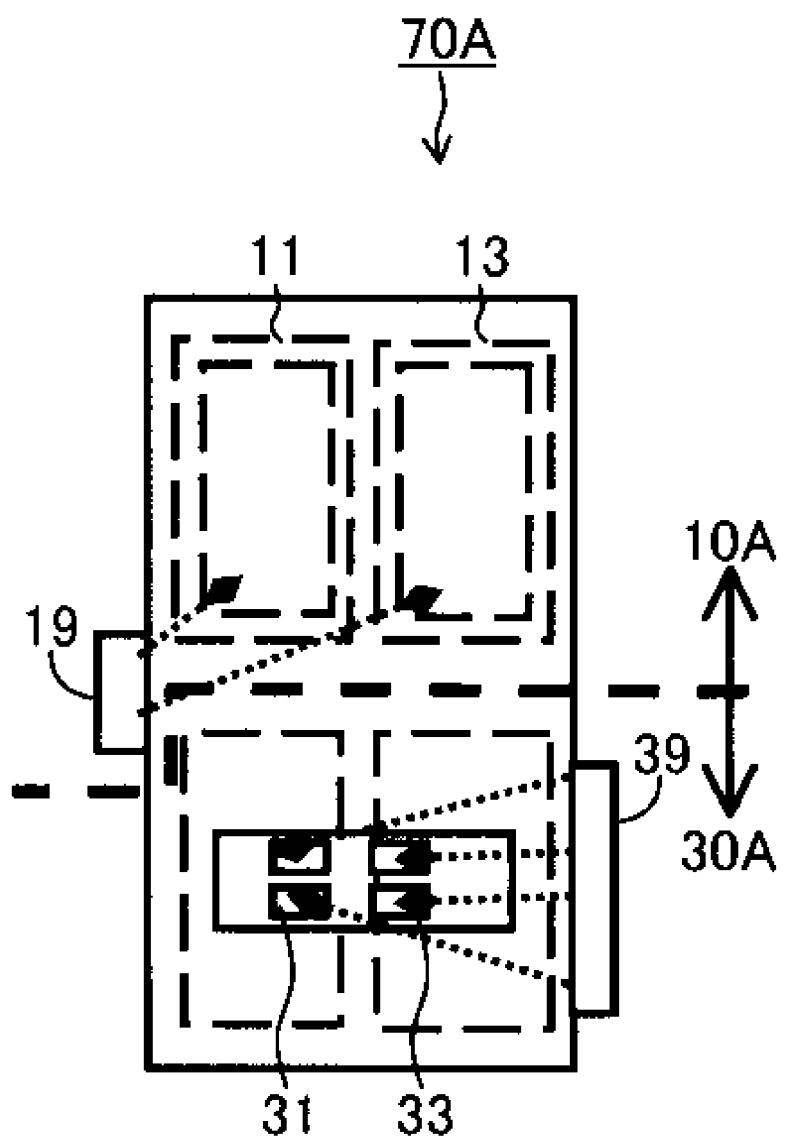
FIG. 12C is a schematic view showing an internal structure when the perspiration acceleration/perspiration collection device according to the fifth preferred embodiment of the present invention is seen from the front surface.
Figure 12D:
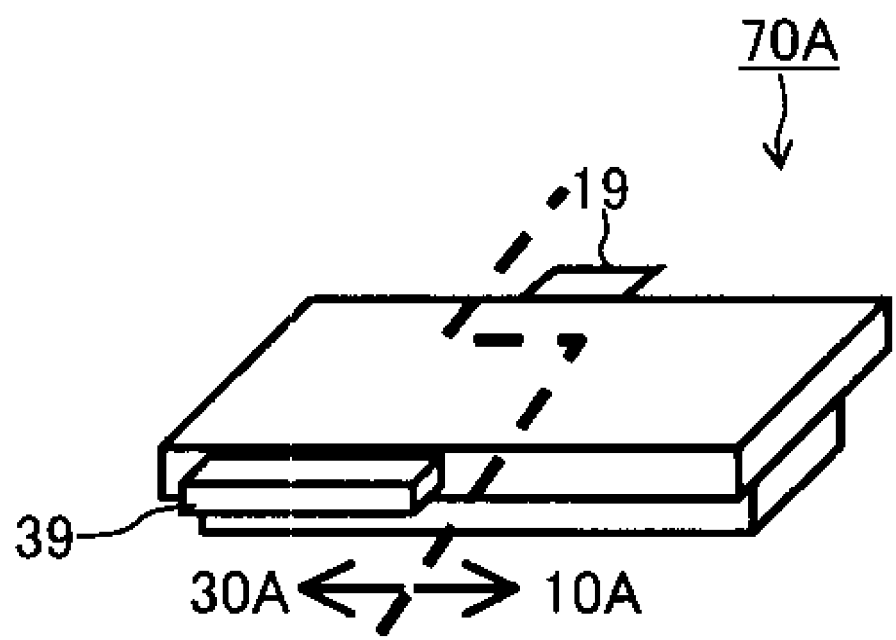
FIG. 12D is a schematic view of the outer appearance when the front surface of the perspiration acceleration/perspiration collection device according to the fifth preferred embodiment of the present invention is seen from a diagonal direction.

With reference to FIG. 12C and FIG. 12D, the perspiration acceleration/perspiration collection device 70A according to the fifth preferred embodiment includes the perspiration accelerating unit 10A having the function similar to the perspiration acceleration device 10 according to the first preferred embodiment to the fourth preferred embodiment, and the perspiration collecting unit 30A having the function similar to the perspiration collection device 30. With reference to FIG. 12C, the perspiration accelerating unit 10A includes the introducing electrode 11, the reference electrode 13, and the connector 19, and the terminals of connector 19 are wired to the introducing electrode 11 and the reference electrode 13, respectively. With reference to FIG. 12C, the perspiration collecting unit 30A includes the first component detector 31, the second component detector 33, and the connector 39, and the terminals of the connector 39 are wired to the first component detector 31 and the second component detector 33, respectively.

Furthermore, with reference to FIG. 12C and FIG. 12D, assuming the perspiration acceleration/perspiration collection device 70A is a substantially hexahedron and couples with the electronic component device 50 by being fitted to the frame 59 of the electronic component device 50, the connector 19 and the connector 39 are arranged at the surface (referred to as first surface) of the perspiration acceleration/ perspiration collection device 70A with respect to the electronic component 50 and the surface (referred to as second surface) opposing thereto, respectively, with the perspiration acceleration/perspiration collection device 70A coupled to the electronic component device 50. The connector 19 is arranged on the first surface at a position that can be connected with the connector 54A of the electronic component device 50 when the perspiration acceleration/perspiration collection device 70A is coupled to the electronic component device 50 so that the first surface faces the electronic component device 50. Similarly, the connector 39 is arranged on the second surface at a position that can be connected with the connector 54B of the electronic component device 50 when the perspiration acceleration/perspiration collection device 70A is coupled to the electronic component device 50 so that the second surface faces the electronic component device 50.

In the fifth preferred embodiment, as in the second preferred embodiment, the connectors 54A, 54B of the electronic component device 50 have functions similar to the switches 52A, 52B according to the first preferred embodiment. In other words, the determination unit 503 of the electronic component device 50 according to the fifth preferred embodiment determines which of the perspiration acceleration device 10 or the perspiration collection device 30 is coupled to the electronic component device 50 by detecting which connectors 54A or 54B, is conducted when a power is distributed to the electrode current generation unit 507 and the detection performance unit 509 in step S101.

With the measurement device 1 according to the fifth preferred embodiment having the above configuration, the control circuit 53 of the electronic component device 50 is wired to the introducing electrode 11 and the reference electrode 13 arranged in the perspiration accelerating unit 10A of the perspiration acceleration/perspiration collection device 70A, so that the perspiration accelerating performance can be made, when the perspiration acceleration/perspiration collection device 70A is coupled to the electronic component device 50 so that the first surface faces the electronic component device 50. The control circuit 53 of the electronic component device 50 is wired to the first component detector 31 and the second component detector 33 arranged in the perspiration collecting unit 30A of the perspiration acceleration/perspiration collection device 70A, so that the perspiration collection and measurement computation performance can be made, when the perspiration acceleration/perspiration collection device 70A is coupled to the electronic component device 50 so that the second surface faces the electronic component device 50. That is, with the measurement device 1 according to the fifth preferred embodiment having the above configuration, the coupling state of the perspiration acceleration/perspiration collection device 70A can be resolved with the electronic component device 50 attached to the measurement site with the belt 2 after coupling the perspiration acceleration/perspiration collection device 70A to the electronic component device 50 and making the perspiration accelerating performance, and the direction of the perspiration acceleration/perspiration collection device 70A may be rotated 180° and coupled to the electronic component device 50 to make the perspiration collection and measurement computation performance. The perspiration thus can be efficiently collected from the same position as the measurement site where the perspiration accelerator is introduced. Furthermore, in the fifth preferred embodiment, the perspiration acceleration device 10 and the perspiration collection device 30 are configured by one device, so that the number of devices can be reduced and the operability of the measurer can be enhanced.

Figure 13A:
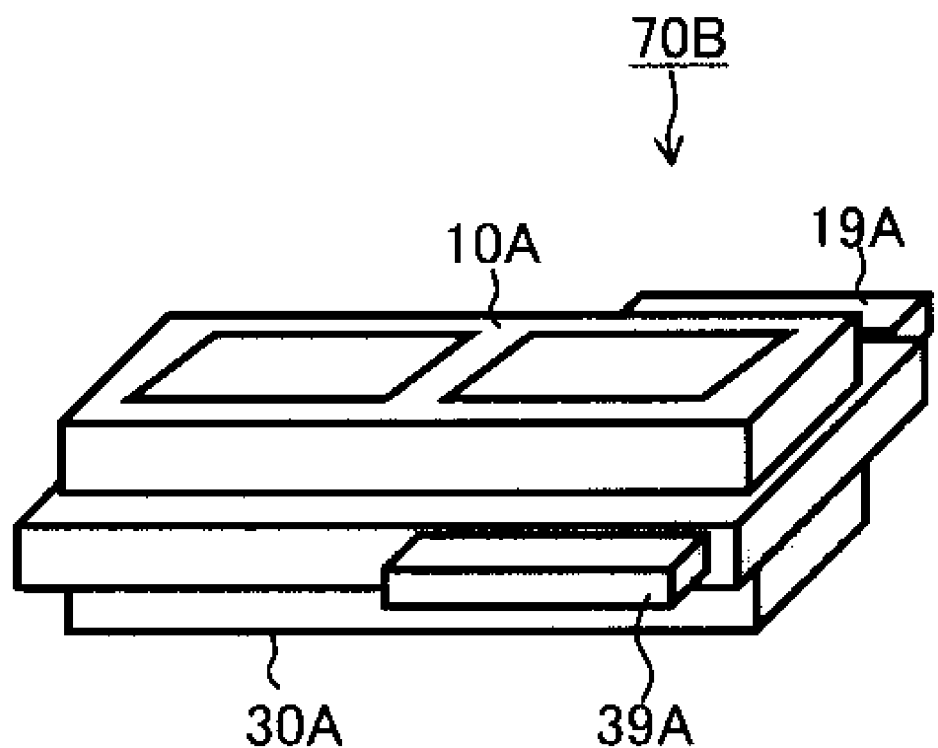
FIG. 13A is a schematic view of an outer appearance when the front surface of the perspiration acceleration/perspiration collection device according to a variation of the fifth preferred embodiment of the present invention is seen from a diagonal direction.
Figure 13B:
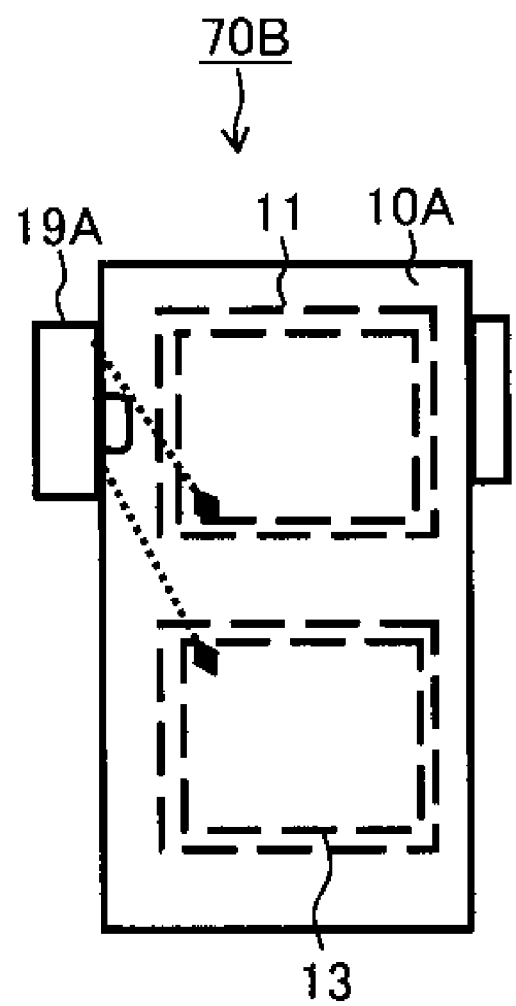
FIG. 13B is a schematic view showing an internal structure when the perspiration acceleration/perspiration collection device according to the variation of the fifth preferred embodiment of the present invention is seen from the front surface.
Figure 13C:
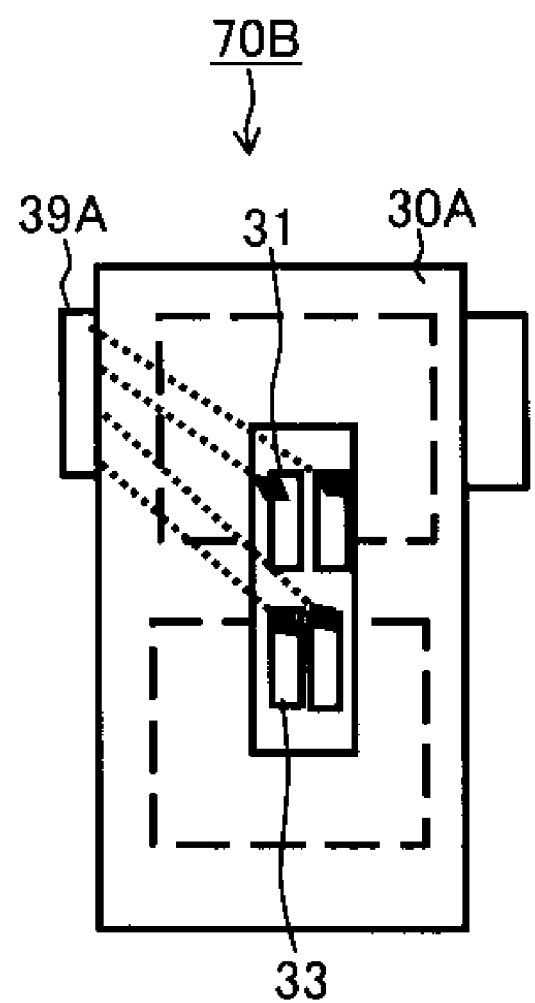
FIG. 13C is a schematic view showing an internal structure when the perspiration acceleration/perspiration collection device according to the variation of the fifth preferred embodiment of the present invention is seen from the back surface.

A method of configuring the perspiration acceleration device 10 and the perspiration collection device 30 with one device is not limited to the above method. For instance, as a variation, a method configuring as shown in FIG. 13A to FIG. 13C may be adopted. Specifically, with reference to FIG. 13A, the perspiration acceleration/perspiration collection device 70B according to the variation has the perspiration accelerating unit 10A having the function similar to the perspiration acceleration device 10 according to the first preferred embodiment to the fourth preferred embodiment, arranged on the front surface side, and the perspiration collecting unit 30A having the function similar to the perspiration collection device 30 arranged on the surface opposing the front surface (back surface). FIG. 13B is a view of the perspiration acceleration/perspiration collection device 70B seen from the front surface, and shows the configuration of the perspiration accelerating unit 10A. FIG. 13C is a view of the perspiration acceleration/perspiration collection device 70B seen from the back surface, and shows the configuration of the perspiration collecting unit 30A. The perspiration accelerating unit 10A and the perspiration collecting unit 30A include the connector 19A and the connector 39A, respectively, similar to the third preferred embodiment. These are arranged on the first surface and the second surface at positions where the distance from the front surface and the distance from the back surface are the same. The connector 19A is arranged at a position that can be connected with the connector 54 of the electronic component device 50 when the perspiration acceleration/perspiration collection device 70B is coupled to the electronic component device 50 so that the first surface faces the electronic component device 50, and the connector 39A is arranged on the second surface at a position that can be connected with the connector 54 of the electronic component device 50 when the perspiration acceleration/perspiration collection device 70B is coupled to the electronic component device 50 so that the second surface faces the electronic component device 50.

With such a configuration, similar to the third preferred embodiment, the determination unit 503 of the electronic component device 50 according to the third preferred embodiment detects which terminal of the first terminal to the fourth terminal of the connector 54C is conducted when a power is respectively distributed to the electrode current generation unit 507 and the detection performance unit 509, and detects that the connected second terminal and the third terminal are short circuit in step S101 to determine that the perspiration acceleration device 10 is coupled to the electronic component device 50. Otherwise, determination is made that the perspiration collection device 30 is coupled.

With the measurement device 1 according to the fifth preferred embodiment having the above configuration, the control circuit 53 of the electronic component device 50 is wired to the introducing electrode 11 and the reference electrode 13 arranged in the perspiration accelerating unit 10A of the perspiration acceleration/perspiration collection device 70B, so that the perspiration accelerating performance can be made, when the perspiration acceleration/perspiration collection device 70B is coupled to the electronic component device 50 so that the perspiration accelerating unit 10A becomes the front surface. The control circuit 53 of the electronic component device 50 is wired to the first component detector 31 and the second component detector 33 arranged in the perspiration collecting unit 30A of the perspiration acceleration/perspiration collection device 70B, so that the perspiration collection and measurement computation performance can be made, when the perspiration acceleration/perspiration collection device 70B is coupled to the electronic component device 50 so that the perspiration collecting unit 30A becomes the front surface. That is, with the measurement device 1 according to the fifth preferred embodiment having the above configuration, the coupling state of the perspiration acceleration/perspiration collection device 70B can be resolved with the electronic component device 50 attached to the measurement site with the belt 2 after coupling the perspiration acceleration/perspiration collection device 70B to the electronic component device 50 and making the perspiration accelerating performance, and the front and back of the perspiration acceleration/perspiration collection device 70B may be reversed and coupled to the electronic component device 50 to make the perspiration collection and measurement computation performance. The perspiration thus can be efficiently collected from the same position as the measurement site where the perspiration accelerator is introduced. Furthermore, in the fifth preferred embodiment, the perspiration acceleration device 10 and the perspiration collection device 30 are configured by one device, so that the number of devices can be reduced and the operability of the measurer can be enhanced.

The preferred embodiments disclosed here are illustrative in all aspects and should not be construed as being exclusive. The scope of the present invention is defined by the claims rather than by the description made above, and meanings equivalent to the claims and all modifications within the scope of the present invention are intended to be encompassed.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A blood component concentration measurement device comprising:
   a first device, provided with a first fitting member, arranged to be placed on a surface of a body at a measurement site and including a perspiration accelerating unit arranged to accelerate perspiration from a surface of a body or a measurement site;
   a second device, provided with a second fitting member having a configuration identical to a configuration of the first fitting member, arranged to be placed on the surface of the body at the measurement site and including a perspiration collecting unit arranged to collect perspiration from the surface of the body or the measurement site;
   a positioning unit arranged to fix positions of the first device and the second device with respect to the measurement site;
   a coupling unit arranged to be removably fitted with either the first device through the first fitting member or the second device through the second fitting member with respect to the positioning unit such that the second device will be placed at a position at the measurement site that is a same position at which the first device was placed and then removed; and
   a third device including the positioning unit and the coupling unit and being a separate body from the first device and the second device; wherein
   the first device and the second device respectively have positions thereof fixed with respect to the surface of the body or the measurement site while contacting the measurement site, by being coupled with respect to the positioning unit arranged in the third device with the coupling unit; and
   the third device further includes:
      a determination unit arranged and programmed to determine which one of the first device and the second device is coupled by the coupling unit;
      a measurement unit arranged to measure a perspiration concentration of the target component detected by the second device;
      a conversion unit arranged to convert the perspiration concentration of the target component to a blood concentration; and
      an output unit arranged to output the blood concentration of the target component.

2. The blood component concentration measurement device according to claim 1, wherein
   the second device further includes a detector arranged to detect a target component from the perspiration collected by the perspiration collecting unit; and
   the third device further includes:
      a first control unit arranged to control the perspiration accelerating performance in the perspiration accelerating unit of the first device, when it is determined that the first device is coupled by the coupling unit; and
      a second control unit arranged to control detection performance of the target component in the detector of the second device, when it is determined that the second device is coupled by the coupling unit.

3. The blood component concentration measurement device according to claim 1, wherein
   the first device and the second device are integrally formed.

4. The blood component concentration measurement device according to claim 2, wherein
   the first control unit is arranged to control the perspiration accelerating performance in the perspiration accelerating unit of the function of the first device when it is determined that the coupling state of the first device and the second device is in a first state;
   the second control unit is arranged to control the detection performance of the target component in the detector of the function of the second device when it is determined that the coupling state of the first device and the second device is in a second state; and
   the first state and the second state have a relationship in which a surface of the first device and the second device facing the third device differs, when coupled to the positioning unit of the third device by the coupling unit.

5. The blood component concentration measurement device according to claim 2, wherein
   the first control unit is arranged to control the perspiration accelerating performance in the perspiration accelerating unit of the function of the first device when it is determined that the coupling state of the first device and the second device is in a first state;
   the second control unit is arranged to control the detection performance of the target component in the detector of the function of the second device when it is determined that the coupling state of the first device and the second device is in a second state; and
   the first state and the second state have a relationship in which a surface of the first device and the second device facing the surface of the body or the measurement site differs, when coupled to the positioning unit of the third device by the coupling unit.

6. The blood component concentration measurement device according to claim 1, wherein the first device further includes:
   an operation unit arranged to accept an operation instructing a start of the perspiration accelerating performance; and
   a control unit arranged to control the perspiration accelerating performance when the operation is made; and
   the second device further includes:
   a detector arranged to detect a target component from the perspiration collected by the perspiration collecting unit;
   an operation unit arranged to accept an operation to start the detection in the detector;
   a control unit arranged to control the detection performance in the detector when the operation is made;
   a measurement unit arranged to measure a perspiration concentration of the target component;
   a conversion unit arranged to convert the perspiration concentration of the target component to a blood concentration, and
   an output unit arranged to output the blood concentration of the target component.

7. A control method of a blood component concentration measurement device which includes a first device, provided with a first fitting member, arranged to be placed on a surface of a body at a measurement site and including a perspiration accelerating unit arranged to accelerate perspiration from a surface of a body or a measurement site, a second device, provided with a second fitting member having a configuration identical to a configuration of the first fitting member, arranged to be placed on the surface of the body at the measurement site and including a perspiration collecting unit arranged to collect perspiration from the surface of the body or measurement site and a detector arranged to detect a target component from the perspiration collected by the perspiration collecting unit, and a third device including a positioning unit arranged to fix positions of the first device and the second device with respect to the measurement site, and a coupling unit arranged to be removably fitted with either the first device through the first fitting member or the second device through the second fitting member with respect to the positioning unit such that the second device will be placed at a position at the measurement site that is a same position at which the first device was placed and then removed, the method comprising the steps of:

determining which one of the first device and the second device is coupled to the third device by the coupling unit;

controlling the perspiration accelerating performance in the perspiration accelerating unit of the first device, when it is determined that the first device is coupled by the coupling unit;

controlling the detection performance of the target component in the detector of the second device, when it is determined that the second device is coupled by the coupling unit;

measuring a perspiration concentration of the target component detected by the second device;

converting the perspiration concentration of the target component to a blood concentration; and outputting the blood concentration of the target component.

\* \* \* \* \*